(12) United States Patent
Shen et al.

(10) Patent No.: US 7,927,790 B2
(45) Date of Patent: Apr. 19, 2011

(54) SUPPRESSION OF HIV-1 REPLICATION VIA INHIBITION OF HUMAN FLAP ENDONUCLEASE-1-MEDIATED HIV-1 CENTRAL DNA FLAP PROCESSING

(75) Inventors: Binghui Shen, Glendora, CA (US); Li Zheng, Temple City, CA (US)

(73) Assignee: City of Hope, Duarte, CA (US)

( * ) Notice: Subject to any disclaimer, the term of this patent is extended or adjusted under 35 U.S.C. 154(b) by 1290 days.

(21) Appl. No.: 11/440,581

(22) Filed: May 24, 2006

(65) Prior Publication Data
US 2006/0281819 A1      Dec. 14, 2006

Related U.S. Application Data

(60) Provisional application No. 60/684,196, filed on May 24, 2005.

(51) Int. Cl.
*C12Q 1/70* (2006.01)
*C12Q 1/68* (2006.01)

(52) U.S. Cl. ............................................... 435/5; 435/6

(58) Field of Classification Search ................ 435/5
See application file for complete search history.

(56) References Cited

U.S. PATENT DOCUMENTS

| | | | |
|---|---|---|---|
| 6,090,543 | A | 7/2000 | Dahlberg et al. |
| 6,348,314 | B1 | 2/2002 | Dahlberg et al. |

FOREIGN PATENT DOCUMENTS

WO      WO 9940227 A1 *    8/1999

OTHER PUBLICATIONS

Bushman, F. D. (1999) Host proteins in retroviral cDNA integration. *Adv. Virus Res*. 52:301-317.
Charneau, P. and Clavel, F. (1991) A single-stranded gap in human immunodeficiency virus unintegrated linear DNA defined by a central copy of the polypurine tract. *J. Virol*. 65:2415-2421.
Charneau, P., et al. (1992) A second origin of DNA plus-strand synthesis is required for optimal human immunodeficiency virus replication. *J. Viol*. 66:2814-2920.
Charneau, P., et al. (1994) HIV-1 reverse transcription. A termination step at the center of the genome. *J. Mol. Biol*. 241:651-62.
Chen, H., and Engelman, A. (1998) The barrier-to-autointegration protein is a host factor for HIV type 1 integration. *Proc. Natl. Acad. Sci*. USA. 95:15270-15274.

(Continued)

*Primary Examiner* — Shengjun Wang
(74) *Attorney, Agent, or Firm* — Perkins Coie LLP; Lauren Sliger

(57) ABSTRACT

FEN-1 is involved in processing HIV central DNA flap (CDF) and is a target for intervention of HIV-1 replication. Inhibition of HIV-1 CDF removal by expression of D181A FEN-1 mutant suppresses viral DNA replication, further demonstrating that FEN-1 is a target. Methods of identifying and using molecules that inhibit FEN-1 processing HIV-1 CDF and other methods of inhibiting FEN-1 processing are provided. Useful small molecules specifically suppress FEN-1 cleavage of HIV CDF but have little effect on FEN-1's function in RNA-DNA primer removal. Pentamidine inhibits HIV replication by suppressing FEN-1-mediated HIV-CDF processing.

15 Claims, 16 Drawing Sheets

OTHER PUBLICATIONS

Decker, T., and M. L. Lohmann-Matthes. (1988) A quick and simple method for the quantitation of lactate dehydrogenase release in measurements of cellular cytotoxicity and tumor necrosis factor (TNF) activity. *J Immunol. Methods* 115:61-9.

Doranz, B.J., Bail, S.S. et al., (1999) Use of a gp120 binding assay to dissect the requirements and kinetic of human immunodeficiency virus fusion events. *J. Viol.* 73:10346-10258.

Dvorin, J. D., Bell, P., Maul, G. G., Yamashita, M., Emerman, M., and Malim, M. H. (2002) Reassessment of the role of integrase and the central DNA flap in human immunodeficiency virus type 1 nuclear import. *J. Virol.* 76:12087-12096.

Farnet, C. M., and Bushman, F. D. (1997) HIV-1 cDNA integration: requirement of HMG 1(Y) protein for function of preintegration complexes in vitro. *Cell* 88:483-492.

Farnet, C. M., and Haseltine, W. A. (1990) Integration of human immunodeficiency virus type 1 DNA in vitro. *Proc. Natl. Acad. Sci. USA* 87:4164-4168.

Farnet, C.M. and Haseltine, W.A. (1991) Determination of viral proteins present in the human immunodeficiency virus type 1 preintegration complex. *J. Viol.* 65:1910-1915.

Faust, E. A. and Triller, H. (2002) Stimulation of human flap endonuclease 1 by human immunodeficiency virus type 1 integrase: Possible role for flap endonuclease 1 in 5'-end processing of human immunodeficiency virus type 1 integration intermediates. *J. Biomedical Science* 9:273-287.

Gaur, M., and A. D. Leavitt (1998). Mutations in the human immunodeficiency virus type 1 integrase D,D(35)E motif do not eliminate provirus formation. *J. Virol.* 72:4678-85.

Harrington, J.J. and Lieber, M. R. (1994) Functional domains within FEN-1 and RAD2 define a family of structure-specific endonucleases: implications for nucleotide excision repair. *Genes & Development* 8:1344-1355.

Harrington, J.J. and Lieber, M. R. (1994) The characterization of a mammalian DNA structure-specific endonuclease. *EMBO J.*13(5):1235-1246.

Hiraoka, L.R., et al., (1995) Sequence of Human FEN-1, a Structure-Specific Endoneuclease, and Chromosomal Localization of the Gene (*FEN1*) in Mouse and Human. *Genomics* 25:220-225.

Ho, D. D., et al. (1991) Conformational epitope on gp120 important in CD4 binding and human immunodeficiency virus type 1 neutralization identified by a human monoclonal antibody. *J Virol.*, 65:489-93.

Hungnes, O., et al. (1992) Mutations in the central polypurine tract of HIV-1 result in delayed replication. *Virology* 190:440-442.

Kao, H.-I., and Bambara, R. A. (2003) The protein components and machanism of eukaryotic Okazaki fragment maturation. *Critical Reviews in Biochemistry and Molecular Biology* 38:433-452.

Kucherlapati, M., et al. (2002) Haploinsufficiency of flap endonuclease (Fen-1) leads to rapid tumor progress. *Proc. Natl. Acad. Sci. USA* 99:9924-9929.

Lieber, M.R. (1997) The Fen-1 family of structure-specific nucleases in eukaryotic DNA replication, recombination and repair. *BioEssays.* 19:233-240.

Limón, A., et al. (2002) Wild-type levels of nuclear localization and human immunodeficiency virus type 1 replication in the absence of the central DNA flap. *J. Virol.* 76:12078-12086.

Miller, M. D., et al. (1995) Human immunodeficiency virus type 1 preintegration complexes containing discontinuous plus strand are competent to integrate in vitro. *J. Virol.* 69:3938-3944.

Miller, M. D., et al. (1997) Human immunodeficiency virus type 1 preintegration complexes: studies of organization and composition. *J. Virol.* 71:5382-5390.

Murante, R.S., et al. (1995) Calf 5' to 3' exo/endonuclease must slide from a 5' end of the substrate to perform structure-specific cleavage. *J. Biol. Chem.* 270:30377-83.

Murray, J.M., et al., (1994) Structural and Functional Conservation of the Human Homolog of the *Schizosaccharomyces ponbe rad2* gene, Which Is Required for Chromosome Segregation and Recovery from DNA Damgage. *Molecular and Cellular Biology* 14:4878-4886.

Parrish, J., et al. (2003) CRN-1, a *Caenorhabditis elegans* FEN-1 homologue, cooperates with CPS-6/EndoG to promot apoptotic DNA degradation. *EMBO J.* 22(13):3451-3460.

Qiu, J., et al. (2001) Cell cycle-dependent and DNA damage-inducible nuclear localization of FEN-1 nuclease is consistent with its dual functions in DNA replication and repair. *J. Biol. Chem.* 276:4901-4908.

Rumbaugh, J.A., et al. (1998) Processing of an HIV replication intermediate by the human DNA replication enzyme FEN1. *J. Biol. Chem.* 273:28740-5.

Sharma, P. L., and Crumpacker, C. S. (1999) Decreased processivity of human immunodeficiency virus type 1 reverse transcriptase (RT) containing didanosine-selected mutation Leu74Val: a comparative analysis of RT variants Leu74Val and lamivudine-selected Met184Val. *J. Virol.* 73:8448-856.

Shen, B., et al. (1996) Essential amino acids for substrate binding and catalysis of human flap endonuclease-1. *J. Biol. Chem.* 271:9173-9176.

Shen, B., et al. (1998) Flap endonuclease homologues in archaebacteria exist as independent proteins. *TiBS*. 23:171-173.

Shibata, Y., and Nakamura, T. (2002) Defective flap endonuclease 1 activity in mammalian cells is associated with impaired DNA repair and prolonged S phase delay. *J. Biol. Chem.* 277:746-754.

Stevenson, M. (2000) HIV nuclear import: What's the flap? *Nat. Med.* 6:626-8.

Whitwam, T., et al. (2001) Identification of a central DNA flap in feline immunodeficiency virus. *J. Virol.* 75:9407-14.

Yam, P. Y., et al. (2002) Design of HIV vectors for efficient gene delivery into human hematopoietic cells. *Mol. Ther.* 5:479-84.

Yoder, K.E., and Bushman, F.D. (2000) Repair of gaps in retroviral DNA integration intermediates. *J. Virol.* 74:11191-11200.

Zennou, V., et al. (2000) HIV-1 genome nuclear import is mediated by a central DNA flap. *Cell* 101:173-85.

Zennou, V., et al. (2001) The HIV-1 DNA flap stimulates HIV vector-mediated cell transduction in the brain. *Nat. Biotechnol.* 19:446-50.

Zheng, L., et al. (2004) Novel function of the flap endonuclease-1 complex in processing stalled DNA replication forks. *EMBO Reports* 6:83-89.

\* cited by examiner

A.

B.

C.

D.

1. CEM/HIV NL4-3

3. CEM-D181A/HIV NL4-3

2. CEM-FEN-1/HIV NL4-3

4. CEM

1. CEM/HIV IIIB

3. CEM-D181A/HIV IIIB

2. CEM-FEN-1/ HIV IIIB

4. CEM

| Pentamidine (mM) | 0 | 0.4 |
|---|---|---|
| $K_m$ (nM) | 0.22 | 0.034 |
| $K_{cat}$ (min$^{-1}$) | 0.73 | 0.01 |

A.

B.

A.

B.

SEQUENCE LISTING

```
<160> NUMBER OF SEQ ID NOS: 1

<210> SEQ ID NO 1
<211> LENGTH: 6
<212> TYPE: DNA
<213> ORGANISM: Artificial
<220> FEATURE:
<223> OTHER INFORMATION: Restriction enzyme recognition sequence

<400> SEQUENCE: 1 ctggag                                                              6
```

SUPPRESSION OF HIV-1 REPLICATION VIA INHIBITION OF HUMAN FLAP ENDONUCLEASE-1-MEDIATED HIV-1 CENTRAL DNA FLAP PROCESSING

RELATED APPLICATIONS

The present application is related to and claims priority under 35 U.S.C. §119(e) to U.S. provisional patent application Ser. No. 60/684,196, filed May 24, 2005, which is incorporated by reference herein in its entirety.

GOVERNMENT INTEREST

The research in the present application was supported, in part, by NIH/NCI Grant No. 2R01CA073764. The Government may have certain rights in the invention.

BACKGROUND

Each of the references cited herein is incorporated by reference in its entirety. A complete listing of the citations is set forth at the end of the specification.

Retroviruses, such as HIV, replicate via a complex life cycle during which the viral genome undergoes a series of structural transformations. To initiate the infection cycle, the parental virus attaches to a specific receptor on the surface of a susceptible cell, leading to fusion and entry of the viral core. Fusion initiates within five minutes at physiological temperatures and is completed in about three hours (Doranz 1999). Once a retrovirus has entered the cell, it must traverse the cytoplasm, moving from the cell periphery to the nucleus.

Retroviral core RNA undergoes reverse transcription, generating a double-stranded DNA copy of the RNA genome. A defined characteristic of the preintegration complex (PIC) is its ability to mediate integration of the viral DNA through the action of integrase. The large HIV-1 PIC (80-320S) is reported to contain matrix (MA), viral protein R (VPR), reverse transcriptase (RT), nucleocapsid (NC), integrase (IN), as well as other viral encoded and cellular proteins (Farnet 1991). The composition, structure, and metamorphosis of the intracellular forms of an infecting virus remain the least well-characterized aspects of the viral life cycle (Coffin 1997) and create problems when attempting to design effective strategies and compounds to combat HIV. Any discovery that further explains one or more of these aspects of the infecting virus is greatly beneficial.

The next step in the HIV life cycle involves integration via reverse transcription of viral DNA into the host chromosome. Viral integration accounts for the ability of retroviruses to cause productive infection. The integrated provirus can thereafter be expressed as a stable genetic element of the host genome and serve as the template for the next generation of viral RNA (Coffin 1997). Reverse transcription of the plus-strand DNA during HIV reverse transcription is synthesized as two discrete segments, each encoding half of the viral genome. When the upstream-plus strand synthesis takes place during the second strand transfer, elongation proceeds until it reaches the central termination site (CTS), causing a discrete strand displacement termed the "central DNA flap" (CDF).

The CDF, a triple-stranded cDNA intermediate of viral transcription, is created during the terminal step of HIV-1 reverse transcription and corresponds exactly to the 99 nucleotides that separate the central polypurine tract (cPPT) and the CTS (FIG. 1). The CDF functions as a cis-acting determinant for the nuclear import of the HIV-1 genome (Stevenson 2000; Zennou 2000; Whitwam 2001; Zennous 2001). For HIV replication, it is necessary to remove the CDF to complete integration of the viral genome, as well as to retain a functional integrase gene (Bushman 1999). The biological role of this central DNA flap for the nuclear entry of PIC, HIV replication, and infectivity is controversial, as indicated by recent studies (Hungnes 1992; Charneau 1992; Charneau 1994; Stevenson 2000; Zennou 2000; Whitwam 2001; Zennous 2001; Dvoin 2002; Limon 2002).

Human flap endonuclease-1 (FEN-1), a nucleic acid substrate structure-specific nuclease, possesses 5' flap endonuclease (FEN) and nick-specific exonuclease (EXO) activities, which removes initiator RNA from Okazaki fragments during lagging strand DNA synthesis and DNA fragment containing lesions in human cells (Lieber 1997; Rumbaugh 1998; Shen 1998; Kao 2004), as well as gap endonuclease (GEN) activity. To make an endonucleolytic cleavage, it recognizes the 5'-end of an unannealed flap and tracks along the single strand to the point of cleavage, near the position of annealing (Murante 1995). The enzyme also requires an upstream-annealed strand with a free 3'-OH end immediately adjacent to the site of cleavage (Faust 2002; Kucherlapati 2002).

Current anti-HIV drugs all target viral enzymes, but this method lacks long-term effectiveness because the HIV reverse transcriptase does not have a proof-reading function such as those in cellular DNA polymerases. Thus, the HIV strain soon becomes drug-resistant due to the high mutation rate of the viral enzymes. Any effective method for hindering HIV replication by targeting a less mutable, non-viral enzyme would be highly valuable for stable, long-term treatment of the disease (Farnet 1990; Charneau 1991; Miller 1995; Shen 1996; Farnet 1997; Miller 1997; Chen 1998; Sharma 1999; Yoder 2000; Qiu 2001; Shibata 2002; Zheng 2005).

The problems identified herein in the prior art are not all the problems in the prior art. The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In certain embodiments, a method is provided for disrupting retroviral replication by interfering with the processing and repair of the central DNA flap (CDF). The retrovirus may be a lentivirus, such as HIV, or may be an oncovirus or spumavirus. The method employs a substance for use in disrupting retroviral replication, which may be pentamidine or another disrupting substance. The substance may be introduced via external administration or may be endogenously produced by the cell or subject. By preventing CDF processing, the viral genome is prevented from obtaining a functional integrase gene, since the triple-stranded cDNA region encodes the integrase enzyme. Because the integrase gene is essential for normal replication of the HIV genome, processing of the flap occurs before integration of the HIV cDNA into the host genome and is a critical step for HIV replication. Thus, blocking CDF processing halts the replication of HIV. Methods for discovering and designing substances effective to halt the replication of HIV and other retroviruses are also taught.

In certain embodiments, a method is provided for preventing CDF processing by regulating FEN-1 in the PIC, thereby preventing HIV proliferation. FEN-1 is responsible for processing of the central DNA flap. It is demonstrated that FEN-1 enters the PIC, associates with viral components including HIV-1 integrase and reverse transcriptase, and processes the CDF in PICs. FEN-1 may be regulated via the expression of a dominant negative protein, created by a point mutation or other means, that competitively binds to the CDF, or by other known methods for controlling enzymes or proteins in vivo.

In addition to the exemplary aspects and embodiments described above, further aspects and embodiments will become apparent by reference to the drawings and by study of the following descriptions.

BRIEF DESCRIPTION OF THE FIGURES

FIG. 2A is a depiction of the HIV 5' central DNA flap (CDF) structure as the substrate for FEN-1, and a gel showing that the FEN-1 point mutant D181A can efficiently suppress wild type FEN-1 activity in vitro in a concentration ratio of 1:8 between wild type and D181A proteins. CDF substrates ($S_{HIVflap}$) are labeled with $^{32}P$ at the 3' end of the CDF strand. FIG. 2B shows that FEN-1 cleavage is HIV substrate specific and would not cleave host substrate. D181A fails to inhibit FEN-1 cleavage of 5' flap structures with a 3' single nucleotide overhang, which resemble the in vivo RNA primer substrates for FEN-1. d-flap substrates ($S_{d-flap}$) are labeled with $^{32}P$ at the 3' end of the flap strand. Cleavage of d-flap substrates results in products of 40 nt ($P_{d-flap}$).

FIG. 4A is a drawing of plasmid DNA vectors, which randomly insert into the host genome, for expressing c-myc-tagged products. FIG. 4B is an image of a gel showing the results of RT-PCR to detect the plasmid vector (LaP), c-myc-tagged hFEN-1 (LaF) or D181A(LaD). Cells transfected with the empty vector are shown as LaP. FIG. 4C is a chart and an image of endogenous RT activity. Shown is RT activity for three days after virus infection. One ml of supernatant medium from each cell line assayed was used. FIG. 4D: Over-expression of C-myc-tagged wild type FEN-1 and D181A in CEM cells. Endogenous (Endo.) and exogenous (Exo.) FEN-1 proteins in whole cell extracts were detected by Western blot with anti-FEN-1 or anti-C-myc antibodies.

FIG. 13A is a bar chart illustrating the results of inhibition of HIV IIIB replication by pentamidine. H9 cells or CEM cells were challenged with HIV IIIB virus in the absence (PC) or presence of 15 µM pentamidine (PTD) or 10 µM AZT. Cells were grown for 7 days and the concentration of p24 were determined and the inhibition percentage were calculated. FIG. 13B: H9 cells or CEM cells were challenged with HIV IIIB virus in the absence or presence of varying concentration of pentamidine (PTD) or AZT. Cells were grown for 7 days and the concentration of p24 were determined.

DETAILED DESCRIPTION

Figure 1:
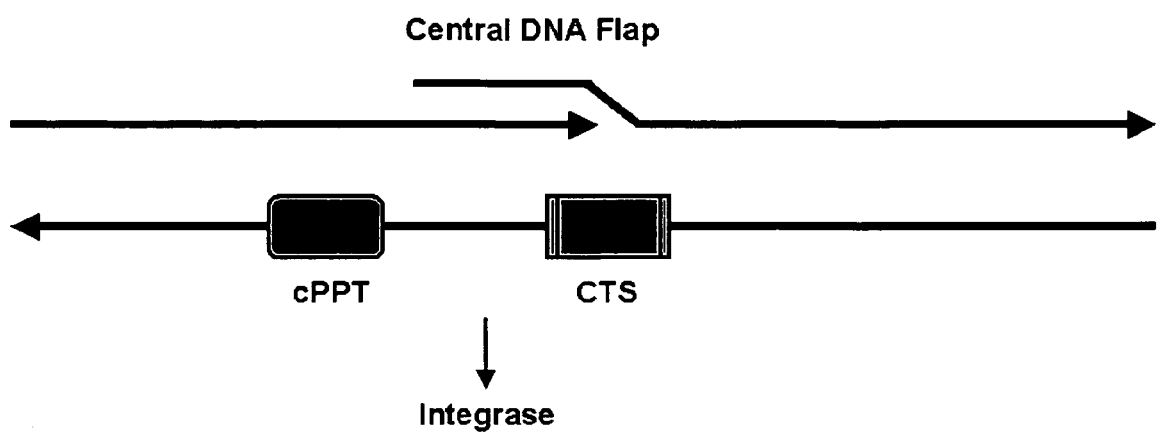
FIG. 1 shows the central DNA flap, which is formed during the terminal step of reverse transcription of the HIV genome. The DNA region shown is part of the open reading frame for integrase. cPPT is the central polypurine tract. CTS is the central termination site.

The methods described herein relate to the discovery that the central DNA flap structure (CDF) is an intermediate product of the HIV life cycle and must be processed to convert the triple-stranded CDF into a double strand. This conversion allows the viral genome to obtain a functional integrase gene, since the triple-stranded cDNA region encodes the integrase enzyme, which is essential for normal replication of the HIV genome. Processing of the flap occurs before integration of the HIV cDNA into the host genome and is a critical step for HIV replication. It has also been discovered that the cellular nuclease FEN-1 is responsible for processing of the central DNA flap. This discovery has been used to design compounds and methods relating to the inhibition of HIV replication.

In one aspect, a method of inhibiting HIV replication by inhibiting processing or repair of the central DNA flap is provided. An inhibiting substance, which may be pentamidine, suppresses FEN-1 cleavage of the CDF structure. A therapeutically effective dose of the substance is administered the cell, tissue, organ, or subject in need of treatment. Preferably, the substance is administered in a pharmaceutically acceptable carrier and may be administered through any effective route, including inhalation.

The methods taught herein, while specifically discovered using HIV, are equally applicable to any retrovirus, including lentiviruses, oncoviruses, and spumaviruses, or any other virus having a CDF or FEN-1 cleavage of any nucleic acid structure. Thus, these methods may be used to inhibit any detrimental retrovirus. Conversely, the methods may be used to aid the processing of the CDF and promote any desirable retrovirus, such as a retroviral vector being used for gene therapy.

In another aspect, mutants of FEN-1, which exhibit a dominant negative effect, are contemplated for use in controlling HIV or other viral replication. The dominant negative FEN-1 mutant, which may be D181A FEN-1, competitively binds the CDF and prevents its processing and repair. The mutant may be therapeutically administered in an effective amount to a subject in need thereof or may be created via gene therapy. If gene therapy is used to create the necessary mutation in FEN-1, the mutant FEN-1 genes are introduced into the subject through known means including, but not limited to, lentiviral or retroviral vectors. As stated above, retroviral vector processing may be controlled using methods described herein, which would likely be a multistep process in which the genes for the dominant negative mutant were introduced into the host genome. The dominant negative protein would then be produced and would interfere with further CDF processing.

In the present experiments, human FEN-1 mutant cell lines derived from HeLa and CEM (T-lymphocyte) were established employing a dominant negative FEN-1 mutant, D181A, which binds to the flap DNA tightly but is deficient in catalysis and nuclear localization. The experiments indicate that the mutant protein specifically suppresses wild type FEN-1 function in the cytoplasm and consequently inhibits the replication of HIV-1. The next set of experiments test the mechanism by which FEN-1 processes the CDF and determine the consequences with regard to HIV integration and replication when the cellular function of FEN-1 is eliminated.

The use of a model wherein the FEN-1 gene is deleted entirely and wherein HIV-1 strains with or without the central DNA flap are used to determine whether the HIV-1 with CDF fails to replicate in FEN-1 minus T-cells would not work because FEN-1 is an essential gene for cell division. Due to FEN-1's role in DNA replication, its deletion leads to cellular lethality, rendering a simple deletion model unusable. Thus, another independent aspect is the creation of a DNA construct that over-expresses human FEN-1 dominant negative point mutation (D181A) and also harbors a mutation in nuclear localization signal of the FEN-1 protein. In addition to the dominant negative FEN-1 mutant, D181A, established cell lines in which the c-myc-tagged hFEN-1 or c-myc-tagged D181A mutant protein is constitutively over-expressed in HeLa cells as well as CEM cells (T-lymphocyte) were used to test HIV replication capacity in the cell lines.

Using the novel FEN-1 mutant construct, it was discovered that the mutant protein was over-expressed and entered the pre-integration complexes in cytoplasm but did not enter the nucleus by itself. Therefore, the mutant beneficially binds to the CDF site and inhibits the processing of CDF, thus suppressing HIV replication, but does not affect the cellular growth of the target cell. HIV-1 replication was suppressed by more than 99.9% in a stable T-cell lines that over-expressed the D181Anls FEN-1, by measuring the secreted HIV p24 protein concentrations. Further assays involving detailed molecular events including HIV-1 integration and replication using the DNA construct employ various techniques.

Figure 2:
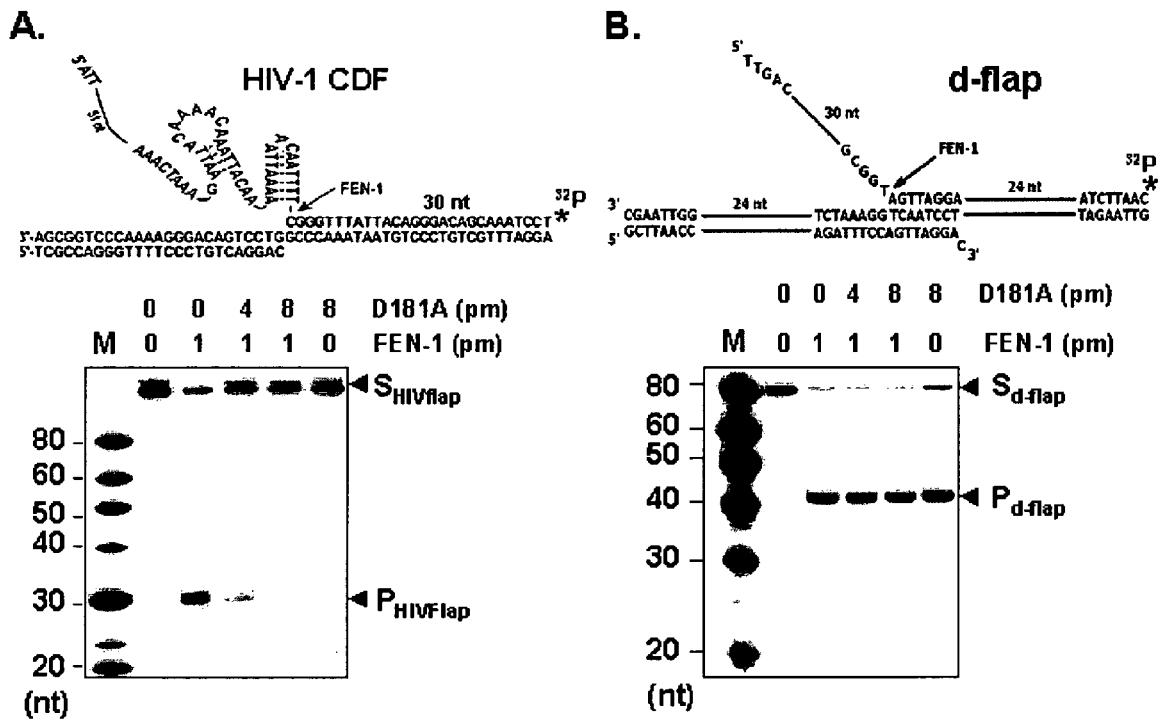
FIG. 2 shows the suppression of FEN-1 activity by a dominant negative point mutant, D181A.

A novel method of identifying a small molecule or class of small molecules to specifically inhibit FEN-1 activity for processing of the HIV-1 CDF, but not cellular DNA replication, is provided. To reach this goal, the creation of a construct that circumvented the inhibition of flap endonuclease activity, leading to cellular lethality, was required. Even though the CDF has a similar configuration to the displaced RNA primer of Okazaki fragments, it has been discovered that the 99 nucleotides of CDF will form two stem loop structures, while the majority of displaced RNA primers will not form this structure during normal cellular DNA replication (FIG. 2). Cleavage of regular 5' flap structures needs only FEN-1's flap endonuclease activity, while cleavage of the CDF structures requires both FEN-1's flap endonuclease and gap endonuclease activities. These two activities of FEN-1 can be segregated in certain conditions (Zheng 2005).

A method of searching small molecules that selectively modulate FEN-1 processing or repair of HIV CDF is defined. The modulation desired is typically suppression of HIV. The strain of HIV may be HIV-1 or HIV-2. The method involves incubating an HIV-infected cell with a test substance for a time sufficient to allow the test substance to disrupt the processing or repair of the central DNA flap and detecting whether the test substance has inhibited HIV replication. The test molecules are selected based on a three pronged criteria. The test substance should be a dication organic molecule, comprise at least one aromatic or imidazol group, and be effective in vitro before being tested in vivo. The efficacy of the test substance can be tested using a variety of known methods for testing for viral load, particularly HIV, such as testing the amount of a secreted protein (e.g., p24) by ELISA. Other methods for testing the efficacy of a substance, such as a chromatin immunoprecipitation assay, may also be used. The test substance may be compared to AZT as a metric to measure its effectiveness and may be used alone or in combination with other methods of inhibiting HIV or treating HIV generally.

Employing this method, pentamidine was discovered to inhibit FEN-1 processing of the HIV CDF structures. Advantageously, pentamidine has little effect on FEN-1 cleavage of regular 5' flap structures resembling RNA-DNA primers during DNA replication, so it is remarkably effective in distinguishing between HIV structures and normal DNA processing. The structure of pentamidine is shown in FIG. 9.

Pentamidine or any other inhibiting compound should be administered in a therapeutically effective amount. A "therapeutically effective amount," "dose," or "dosage" as used herein refers to an amount of a composition that produces a desired therapeutic effect, such as temporarily or permanently preventing, treating, or improving a condition or alleviating symptoms or indications associated with a condition. Thus, a therapeutically effective amount of a composition is also sufficient to cause a pharmacological effect. A therapeutically effective amount of a composition need not cause permanent improvement or improvement of all symptoms or indications. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, gender, disease type and stage, general physical condition, responsiveness to a given dosage, and type of medication), and the type of cell in which a nucleic acid is being inserted.

One skilled in the clinical and pharmacological arts will be able to determine a therapeutically effective amount through routine experimentation, namely by monitoring a subject's response to administration of a compound and adjusting the dosage accordingly and may use well-known references such as Remington: The Science and Practice of Pharmacy (Gennaro ed. $20^{th}$ edition, Williams & Wilkins PA, USA) (2000) for further guidance. Dosage of the compound may also be adjusted based on in vitro or animal dosages, showing effective molar concentrations for a given compound and then calculating the dosage for a human subject based on the factors listed above and other physiological and metabolic conversation factors.

Pentamidine or another substance may be administered at any effective dose, including at a concentration of 0.4 mM. The drug may be administered via any effective method. If administered in an aerosolized form, the dose may be between 50 mg and 1 g, between 100-500 mg, or between 250-400 mg. If administered intravenously, a dose of around 4 mg/kg may be used. It may be beneficial to administer pentamidine or another substance slowly and without rapid infusion. It may also be beneficial to hydrate a subject before treatment. In examining the inhibitory efficiency of pentamidine on HIV-1 replication in T-cell lines, there is an inhibitory effect in one cell line that is equivalent to AZT, while the inhibitor effect in another cell line is about 70% that of AZT. However, viral resistance to pentamidine is much lower than AZT because it inhibits a cellular protein instead of viral proteins. Lowered HIV resistance translates into higher effectiveness for the drug. Pentamidine may be administered in connection with other HIV therapies, such as AZT or the highly active anti-retroviral therapy drugs (HAART).

Any compound, such as pentamidine, used to inhibit HIV replication and/or to treat HIV may be administered in a pharmaceutically acceptable carrier and administered to a subject, usually a human, through an effective route of administration. A "pharmaceutically acceptable carrier" as used herein means a pharmaceutically-acceptable material, composition or vehicle, such as a liquid or solid filler, diluent, excipient, solvent or encapsulating material, involved in carrying or transporting a compound from one cell, tissue, organ, or portion of the body, to another cell, tissue, organ, or portion of the body. Each component must be "pharmaceutically acceptable" in the sense of being compatible with the other ingredients of the formulation. It must also be suitable for use in contact with the tissue or organ of humans and animals without excessive toxicity, irritation, allergic response, immunogenecity, or other problems or complications, commensurate with a reasonable benefit to risk ratio.

Pharmaceutically acceptable carriers for a compound are generally known in the art and may include sugars, starches, cellulose, powdered tragacanth, malt, gelatin, talc, excipients, oils, glycols, esters, buffering agents, and other non-toxic compatible substances employed in pharmaceutical formulations.

Formulations suitable for oral administration may be in the form of capsules, cachets, pills, tablets, lozenges, powders, as granules or a paste, as a solution or a suspension in an aqueous or non-aqueous liquid, as an oil-in-water or water-in-oil liquid emulsion, as an elixir or syrup, or as pastilles (using an inert base, such as gelatin and glycerin, or sucrose and acacia), each containing a predetermined amount of a compound as an active ingredient. In addition, the liquid dosage forms may contain inert diluents commonly used in the art.

Formulations for the topical or transdermal administration of an HIV compound include powders, sprays, ointments, pastes, creams, lotions, gels, solutions, patches and inhalants. The active component may be mixed under sterile conditions with a pharmaceutically acceptable carrier, and with any preservatives, buffers, or propellants that may be required.

A "route of administration" for a compound can be by any pathway known in the art, including without limitation, oral, enteral, nasal, topical, rectal, vaginal, aerosol, transmucosal, transdermal, ophthalmic, pulmonary, and/or parenteral administration. A parenteral administration refers to an administration route that typically relates to injection. Parenteral administration includes, but is not limited to, intravenous, intramuscular, intraarterial, intrathecal, intracapsular, infraorbital, intracardiac, intradermal, intraperitoneal, transtracheal, subcutaneous, subcuticular, intraarticular, subcapsular, subarachnoid, intraspinal, via intrasternal injection, and/or via infusion.

"Treatment" of or "treating" HIV via disruption of HIV replication may mean, without limitation, preventing processing of the central DNA flap, inhibiting wild-type FEN-1 activity, administering or generating an endogenous compound that interferes with FEN-1 activity, or administering or generating a compound that competitively inhibits FEN-1 activity.

Another aspect of the invention is a method of treating a human infected with HIV by disrupting HIV replication using a therapeutically effective amount of a substance that interferes with the integrase gene of HIV and/or interferes with the processing of the central DNA flap or FEN-1. The substance may be pentamidine, another small molecule, or any substance that meets the three part test for screening compounds described herein.

EXAMPLES

Example 1

Creation and Characterization of a Fen-1 Mutant

A point mutation was created in FEN-1's catalytic center (D181). It was found that the mutant protein bound to DNA substrate with a high affinity similar to that of the wild type protein, but lost catalytic activity (Shen 1996). This dominant negative point mutant, D181A, inhibits wild type FEN-1 activity efficiently (FIG. 2A). High concentrations (8-10 folds higher than the wild type protein concentration) of the mutant FEN-1 enzyme almost completely inhibit wild type FEN-1 flap.endonuclease activity in vitro. However, the D181A mutant does not inhibit FEN-1 activity with d-flap substrates, a model structure for host cell RNA primer removal (FIG. 2B).

Example 2

FEN-1 Involvement in CDF Removal and Vector Integration

Figure 3:
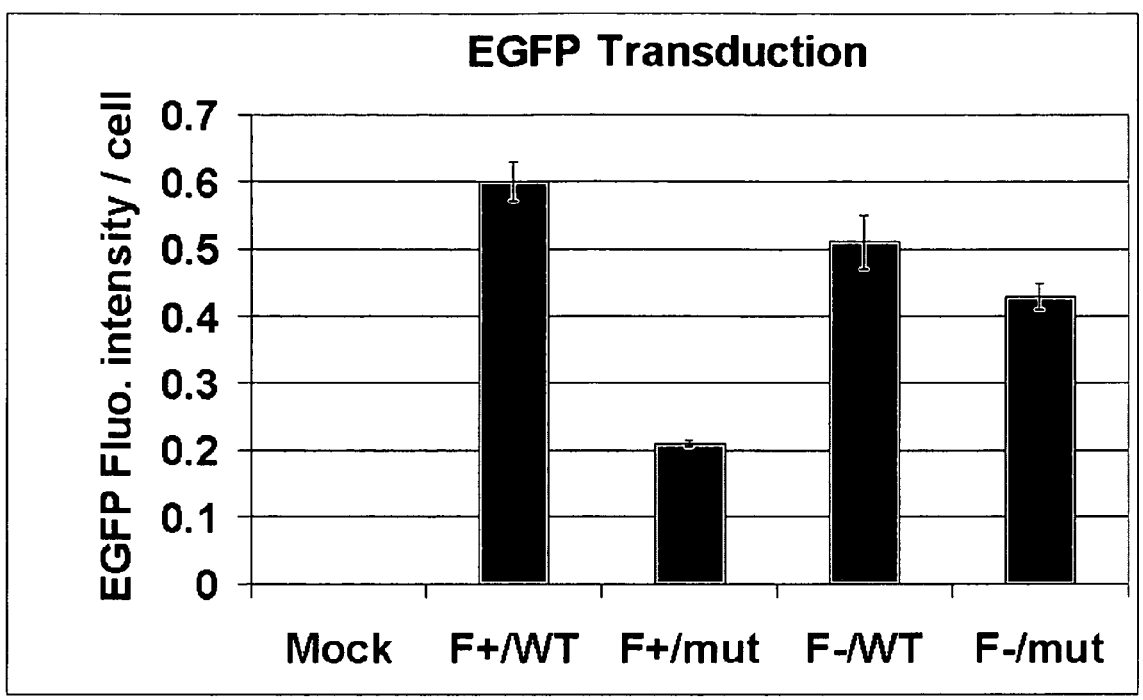
FIG. 3 is a bar graph illustrating the results of an experiment in which human bladder carcinoma T24 cells overexpressing hFEN-1 (WT) and D181A (mut) were treated with tetracycline at a final concentration of 1 µg/ml overnight. The cell was infected with F+/EGFP or F-/EGFP lentivirus vectors for four hours. After changing medium, the cells were cultured for four days. GFP fluorescent signal in the lentivirus-transduced cells was determined in a flow cytometry system and is represented as fluorescent intensity in each cell. Results shown represent the average of three experiments with standard deviations on top of each column.

There is different transduction efficiency of HIV vectors with or without CDF in a human FEN-1 deficient cell line. If removal of CDF by FEN-1 is critical for the HIV-based vector to integrate into the host cell genome, FEN-1 deficiency will affect the integration of HIV vector with CDF, but not that of HIV vector without CDF in the mutant or wild type cells. To test this hypothesis, a cell line derived from human bladder carcinoma that overexpresses the FEN-1 dominant negative mutant D181A under the inducible Tetracycline promoter was used (cell lines from Drs. Yoshiyuki Shibata and Takashi Nakamura, the Department of Radiology and Cancer Biology, Nagasaki University School of Dentistry, 1-7-1 Sakamoto) (Shibata 2002). The function of wild type FEN-1 is suppressed in this cell line, causing cells to grow sick (Shibata 2002). This cell line was infected with the HIV-based vectors HIV7-GFP (Flap$^+$) or HIV6-GFP(Flap$^-$) (Dr. Jiingkuan Yee, Division of Virology, City of Hope), which harbor GFP with or without CDF, respectively. The integration frequency (indicated by the green florescence signals) is suppressed only in FEN-1 deficient cells infected with the vector containing CDF (FIG. 3). This indicates that FEN-1 is involved in CDF removal and consequently in vector integration. Moreover, the green fluorescence signal intensities in wild type and mutant cells infected with vectors without CDF showed no difference, indicating that FEN-1 is not needed for processing of integration intermediates.

Flap positive (F$^+$) and flap (F$^-$) negative lentiviral vectors carrying a gene for green fluorescent protein (F$^+$/GFP and F$^-$/GFP) were generated by plasmid co-transfection as described previously (Yam 2002). About $0.2 \times 10^6$ of the human bladder carcinoma T24 cells were seeded in a 60-cm$^2$ dish. Tetracycline was added to a final concentration of 1 µg/ml to induce the c-myc-tagged hFEN-1 or D181A expression. After a 24 hour induction, cells were exposed to the F$^+$/GFP or F$^-$/GFP retroviral vector at a m.o.i. of 0.1. After a four hour a incubation, the medium was changed. Cells were grown for four more days before being harvested for flow cytometric analysis. GFP gene transduction was analyzed using a flow cytometry system.

Example 3

HIV Replication Is Impaired in FEN-1 Defective Human Fibroblasts (HeLa) and FEN-1 Defective Human T cells (CEM)

Figure 4:
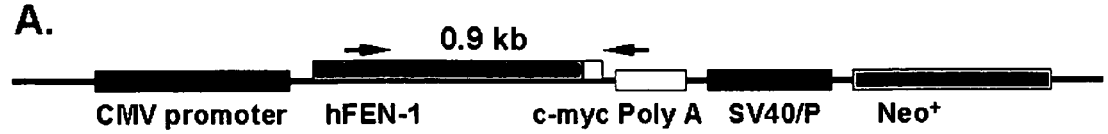
FIG. 4: FEN-1 deficient cell lines and HIV-1 replication.
Figure 4:
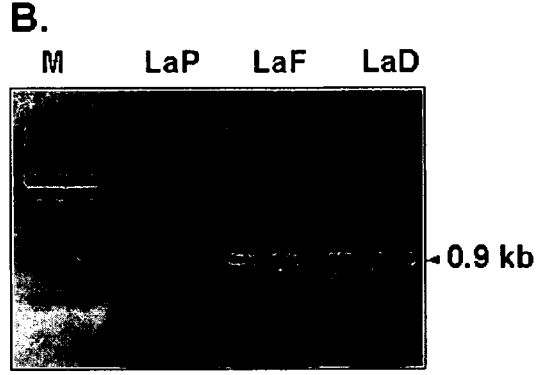
Figure 4:
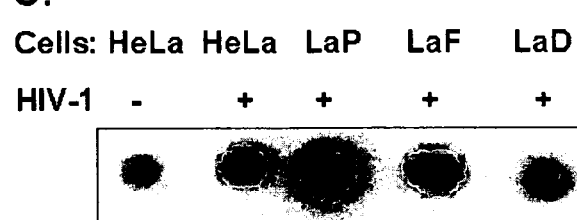
Figure 4:
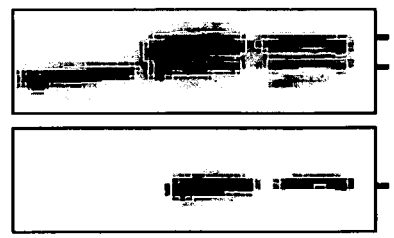

To establish a FEN-1-deficient HeLa cell line and conduct preliminary testing of HIV replication, a new FEN-1 deficient cell line was established that constitutively overexpresses D181A mutant protein with a c-myc-tag in the C-terminus (LaD, see FIG. 4). A cell line that constitutively over-expresses c-myc-tagged wildtype human FEN-1 (LaF) was also generated as described infra. DNA fragments encoding C-myc-fused hFEN-1 or D181A were incorporated into the PLXSN vector (Clonetech), which randomly inserts into the host genome.

HeLa cells have been screened for expression of the exogenous FEN-1 or D181 A with RT-PCR (FIGS. 4B and 4D). The expression of c-myc-tagged hFEN-1 or D181A protein has been examined with RT-PCR and Western blot using either the anti-FEN-1 polyclonal antibody or an anti-c-myc monoclonal antibody. The proteins were overexpressed 3-6 fold more than the endogenous expression. Wild type, empty vector and mutant D181A FEN-1 overexpressing HeLa cell lines (LaF, LaP, and LaD, respectively) are maintained in medium containing G418.

The LaD cell line grew normally, but HIV replication was suppressed. The reason for this unimpaired growth is likely that fusion of c-myc into the C-terminus of FEN-1 disrupted the nuclear localization signaling of the exogenous protein. The cells were able to grow because the endogenous wild type protein was able to migrate into the nucleus to execute its function in DNA replication, while the tagged mutant proteins were only able to enter the cytoplasmic pre-integration complex.

Parental HeLa cells and cells that express the wild type and D181A mutant proteins were infected with a VSV/G-pseudotyped and replication competent HIV-1 virus. In this model system, once stably integrated provirus forms, HIV-1 can only complete one round of replication and newly assembled virions will be released into the supernatant. Therefore, the cell-free, virion-related RT activity correlates with the degree of HIV-1 replication. At two hours post-infection, HIV-1 cDNA was detected in both wild-type and D181A expressing HeLa CD4+ cells at similar levels, suggesting that viral entry and reverse transcription of the RNA were not affected by D181A expression. Three days post-infection, the HIV-1 reverse transcriptase activity, which proportionally represents the replication status, was assayed. HIV replication is inhibited in the cells where the function of FEN-1 is inhibited by over-expression and dominant negativity of the mutant proteins (FIG. 4C).

In order to test the effects of FEN-1 function on HIV replication in its natural host cells, human T-cells, the CEM cells with the same construct shown in FIG. 4A were transfected under selection of G418. CEM cells (C), CEM cells expressing the c-myc-tagged hFEN-1 (F), or D181A mutant (A) were seeded at $0.5 \times 10^4$ cells per well in a 12-well plate. Duplicate plates were prepared for each cell line. The cells were challenged with two HIV-1 strains: NL4-3 and III B. Virus challenge proceeded at both 50 TCID50 and 5 TCID50. The cell culture supernatants were collected and the HIV-1 p24 was measured weekly for four weeks post-infection.

Figure 5:
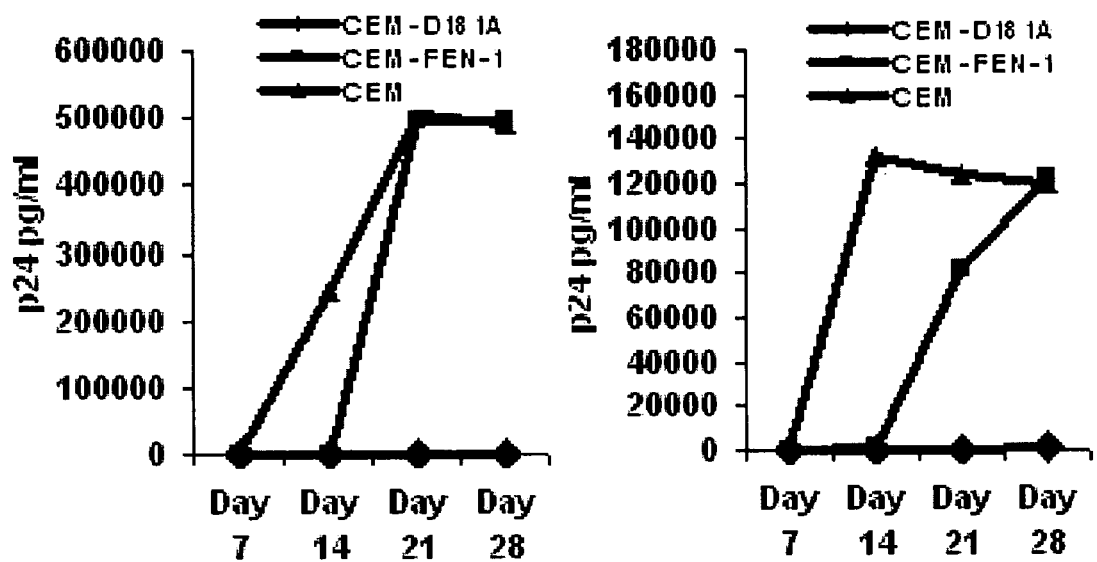
FIG. 5 consists of two line graphs showing that anti-HIV activities were evaluated in the D181A and FEN-1 transduced CEM cells by challenging the cells with two strains of HIV: $HIV_{IIIB}$ and $HIV_{NL4-3}$. Post-infection, the culture supernatant HIV p24 was measured weekly for four weeks. D181A transduced CEM cells showed strong HIV inhibition of both $HIV_{IIIB}$ and $HIV_{NL4-3}$ strains (panel 1 and 2).
Figure 6:
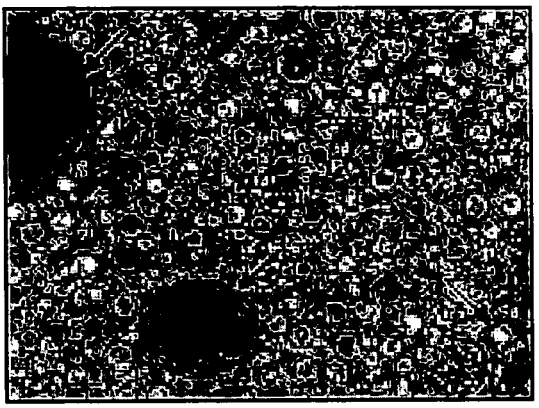
FIG. 6 is a panel of four photographs documenting syncytial formations, which are a cytopathic effect of HIV, found in the $HIV_{IIIB}$ infected CEM cells (panel 1) and CEM cells transduced with wild type FEN-1 (panel 2). In contrast, neither D181A transduced CEM cells (panel 3) nor uninfected CEM cells (panel 4) have syncytial formation.
Figure 6:
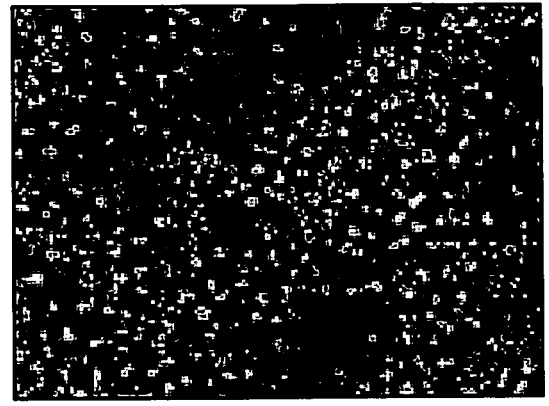
Figure 6:
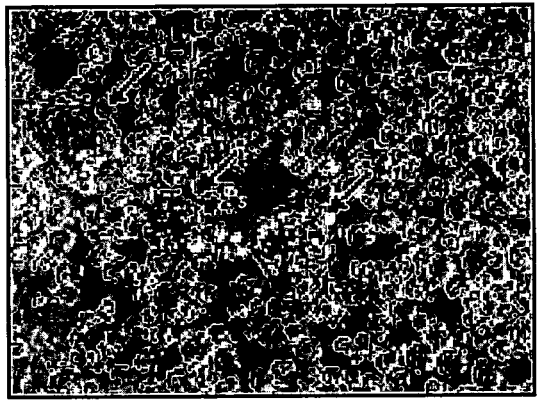
Figure 6:
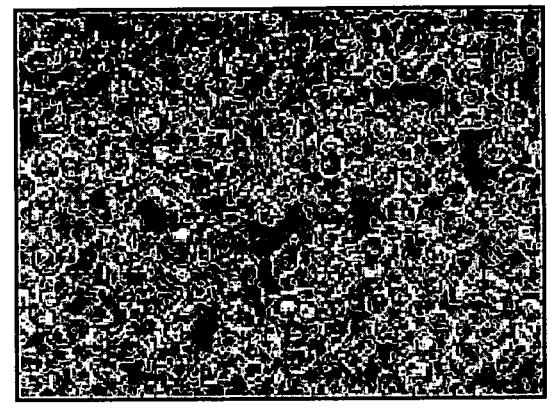
Figure 7:
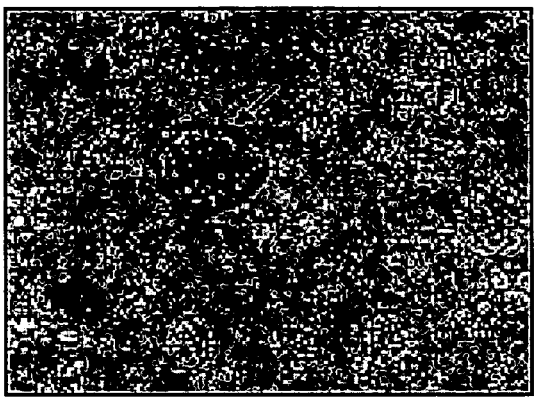
FIG. 7 is another panel of four photographs documenting syncytial formations found in the HIVNL4-3 infected CEM cells (panel 1) and the FEN-1 transduced CEM cells (panel 2), but not found in D181A transduced CEM (panel 3) or uninfected CEM cells (panel 4).
Figure 7:
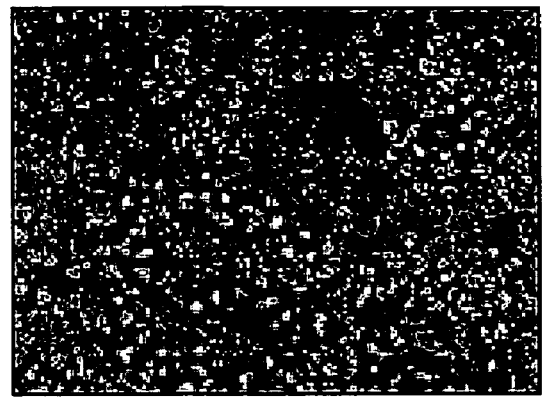
Figure 7:
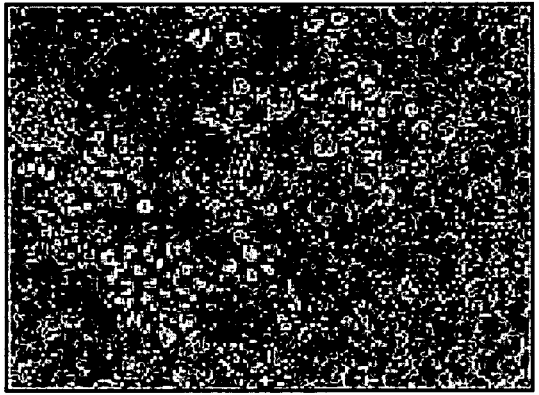
Figure 7:
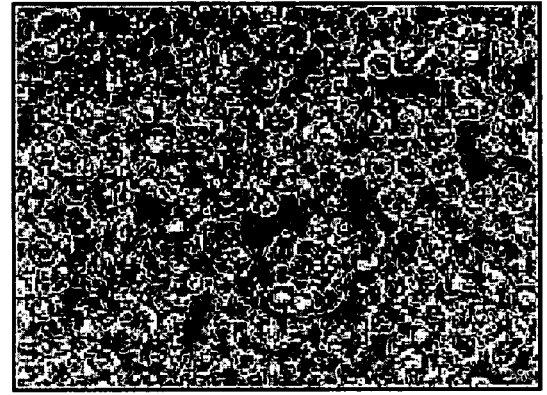

The HIV p24 protein concentration increases one-week post infection in normal CEM cells, while it reached to the same level in FEN-1 overexpressing cells after a delay. In contrast, in the CEM cells with suppression of FEN-1 activity, the HIV p24 protein never increased after 4-weeks post-infection (FIG. 5). Syncytial formation due to the HIV-1 infection was also monitored. Typical syncytial formation were observed in CEM and CEM overexpressing FEN-1 and infection with HIV-1, but not in CEM overexpressing D181A with HIV infection (FIGS. 6 and 7). This illustrates that HIV replication is blocked in FEN-1 defective cells.

Cell lines and culture. $CD4^+$ human CEM lymphocytes were maintained in RPMI 1640 medium plus 10% fetal bovine serum. HeLa, 293T, and PG13 cells (31) were maintained in Dulbecco's modified Eagle's medium (DMEM) supplemented with 10% fetal bovine serum, 100 units/ml penicillin, 100 µg/ml streptomycin at 37° C. in a 5% $CO_2$ incubator. Human T24 bladder carcinoma cells were maintained as described (34).

Establishment of hFEN-1 and D181A over-expression cell lines. C-myc tagged hFEN-1 and D181A retrovirus constructs were generated by inserting the hFEN-1 and D181A PCR fragments into pLXSN vector (Clontech, Calif.). The C-terminal fusion with the c-myc epitope and the mutation in the nucleotides for the $181^{st}$ Ala codon were confirmed with DNA sequencing. The retroviral vectors encoding wt and D181A FEN-1 proteins were generated in PG13 cells. Calcium phosphate precipitation was performed for plasmid DNA transfection. The titer was determined by infecting NIH3T3 cells. Virus-containing supernatants were collected from the selected virus-producing PG13 cell cultures. The supernatants were filtered, and stored at −80° C. To generate HeLa or CEM cells over-expressing c-myc-tagged hFEN-1 or D181A, cells were infected with FEN-1 or D181A retroviral vector ($0.5 \times 10^6$ CFU) by adding the virus-containing supernatant to each well, followed by incubation at 37° C. for 4 hours. After infection, cells were rinsed with fresh medium. Cells were grown and selected in medium containing G418 at a final concentration of 1000 µg/ml for 2 months. Expression of c-myc tagged FEN-1 and D181A were confirmed with Western blotting using anti-c-myc and anti-FEN-1 antibody. T24 cells expressing c-myc tagged FEN-1 and D181A were obtained from Nakamura group of Nagasaki University School of Dentistry and maintained in the presence of blasticidin (final concentration of 6 µg/ml) and Zeocin (final concentration of 30 µg/ml).

Preparation of HIV-1 viral stocks. HIV-1 derived vectors pNL4-3 and pHXB2-Hyg were obtained from Dr. S. A. Chow of University of California, Los Angeles (UCLA). Plasmid DNA was purified with Qiagen's Maxi kit according to the manufacturer's instructions. HIV-1 virus was generated by plasmid co-transfection of 293T cells. The day before transfection, $5.0 \times 10^6$ 293T cells were seeded in 75-$cm^2$ tissue culture flasks. Calcium phosphate precipitation was performed with 10 µg of HIV-1 plasmid DNA and 2 µg of a pCMV-VSV/G expression construct (for expressing the protein G of vesicular stomatitis virus, VSV-G). Supernatants containing viral particles were harvested 36 to 60 hours after transfection. The virus-containing medium was passed through a 0.45 µg pore size filter and stored at −80° C. The titer of viral particles was determined using an HIV-1 p24 ELISA assay kit (Coulter Inc., Miami, Fla.).

HIV-1 replication in CEM cells. CEM cells, or CEM cells infected with the hFEN-1 or D181A retroviral vector, were seeded at $0.5 \times 10^4$ cells per well of a 12-well plate. Duplicate plates were prepared for each cell line. The cells were challenged with HIV-1 strain NL4-3 and III B. Viral challenge was conducted at both 50 TCID50. Cell culture supernatants were collected and the HIV-1 p24 was measured weekly for four weeks post-infection. Syncytium formation due to the HIV-1 infection was monitored, and cells were photographed under a microscope weekly (FIGS. 6-7).

Example 5

Figure 15:
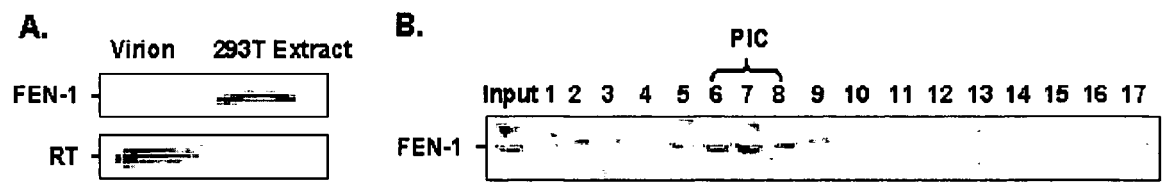
FIG. 15: FEN-1 is not present in virion but is present in PIC in response to HIV-1 infection. (A) Western blotting analysis of FEN-1 and RT in virion and HIV-1-free 293T cellular extracts. (B) Western blotting analysis of FEN-1 in fractions of Nycodenz gradient ultracentrifugation of cytosol extracts of HIV-1-infected HeLa CD4+ cells.

FEN-1 Enters the Preintegration Complex (PIC) and Associates with Viral Components FEN-1 was previously shown to cleave the HIV-1 CDF model structure in vitro, suggesting that the enzyme may participate in processing of CDF in vivo (Rumbaugh 1998). To gain evidence for the role of FEN-1 in CDF processing, FEN-1 is tested to determine whether it is a virion component. Proteins from virion stock prepared in 293T cells were isolated and analyzed by Western blot. FEN-1 is not present in mature virions (FIG. 15A). Because HIV-1 PIC forms after reverse transcription and contains viral proteins and viral cDNA with CDF, it is likely that PIC is responsible for the viral cDNA processing and nuclear localization (Farnet 1991). It is likely that FEN-1 associates with HIV-1 PIC to access the CDF for cleavage. To confirm that cellular FEN-1 physically binds PICs in association with other viral proteins, FEN-1 nuclease removes the CDF in PIC and makes the viral genome ready for integration the following experiments were performed.

Figure 16:
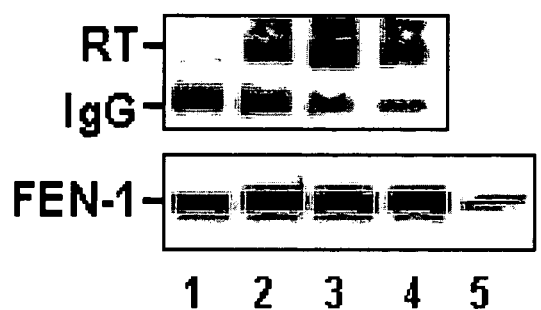
FIG. 16: Co-immunoprecipitation of FEN-1 and HIV-1 RT. (A) Nycodenzy gradient ultracentrifugation fractions 6-8 (PIC fractions), untreated (Lane 1 and 2) or treated with DNase I (Lane 3) or RNase A (Lane 4), were precipitated with anti-FEN-1 antibody (Lanes 2-4) or non-specific IgG (Lane 1, Upper panel). The immunoblot was probed with polyclonal anti-RT antibody (upper panels). The input of FEN-1 is detected with monoclonal anti-FEN-1 antibody. Lane 5 is purified recombinant FEN-1 (Lower panel). (B). PIC fractions were incubated with anti-RT antibody (Lower panel) and the immuno-blot was probed with polyclonal anti-HIV-1 RT antibody or monoclonal anti-FEN-1 antibody (Upper panel).
Figure 16:
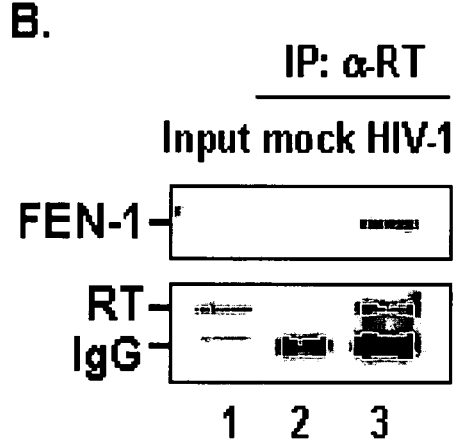

To show that FEN-1 is physically present in PICs with other known PIC components, the HeLa cell lines that over-express hFEN-1 or D181A, described supra, were infected with HIV-1 virus. HIV-1 PICs were isolated from the infected cells by Nycodenz gradient centrifugation (Farnet 1990; Chen 1998; Sharma 1999). The presence of FEN-1 together with viral proteins in PICs was detected by Western blotting analysis using anti-FEN-1 antibody. FEN-1 was detected in gradient fractions 6-8 (FIG. 15B), which contain HIV-1 PICs according to a previous study (Chen 1998). To confirm that FEN-1 associated gradient fractions 6-8 actually contained PIC as reported, these fractions were pooled and enriched by immunoprecipitation using anti-FEN-1 antibody (GeneTex, San Antonio, Tex.). The precipitated protein was then analyzed by Western blot using antibodies to different HIV-1 PIC-specific proteins, including reverse transcriptase (RT), integrase (IN), and Vpr (NIH AIDS Research & Reference Reagent Program). The results revealed that RT was co-precipitated with FEN-1, but not with non-specific rabbit IgG (FIG. 16A), indicating that RT specifically interacted with FEN-1. The association of FEN-1 and RT was not abolished by the treatment of DNase I or RNase A (FIG. 16A), suggesting that the interaction is not mediated by DNA or RNA. Neither HIV-1 IN nor Vpr co-immuno-precipitated with FEN-1. To validate that FEN-1 physically interacts with RT, reciprocal co-immunoprecipitation was conducted using anti-RT antibody. FEN-1 co-immunoprecipitates with RT (FIG. 16B).

Preparation of HIV-1 viral stocks. To prepare virus stocks, plasmid DNA co-transfection was performed using a calcium phosphate precipitation technique (Sambrook 2001). The modified HIV-1 virus was generated by transfecting 293T cells with 10 μg of HIV-1 plasmid DNA, and 2 μg of the pCMV-VSV/G expression construct (for expressing the protein G of the vesicular stomatitis virus, VSV-G). Supernatants containing viral particles were harvested. The titer of viral particles was determined using an HIV-1 p24 ELISA assay. The human HeLa cell lines which overexpress the wild type FEN-1 (LaF) and D181A mutant FEN-1 (LaD), were infected with the modified replication incompetent HIV-1 virus at a multiplicity of infection (m.o.i.) of 10.0. The infected cells were then harvested to isolate PICs.

Isolation of the HIV-1 PIC. PICs are prepared as described previously (Farnet 1990; Farnet 1997; Chen 1998). The harvested infected cells were lysed and nuclei and cell debris removed by successive centrifugations. The resulting supernatant was treated with RNase A to remove RNA contamination and then passed through a 12-ml Sepharose CL-4B spin column. The eluate was purified further by Nycodenz gradient centrifugation. Fractions were collected in successive 300-μl volumes.

Co-immunoprecipitation. PIC fractions were mixed with 50 μl of protein A-agarose beads pre-absorbed with bovine serum albumin to remove non-specific binding proteins. The supernatants were then incubated with 2-5 μg/ml primary antibody (α-FEN-1 or α-RT) 4° C. for 12 hours. The reaction was then mixed with 50 μl of protein A-agarose beads and incubated at room temperature for 1 hour. The beads were washed five times with 1 ml of 1×PBS. The beads were finally resuspended in 50 μl of 1×PBS. 5 μl of the bead suspension was used for each immuno-blotting.

Example 6

FEN-1 Processes the CDF in PICs

Since FEN-1 enters the PICs and physically interacts with viral proteins, it would be reasonable to infer that FEN-1 cleaves the CDF in PICs. The central DNA flap removal makes it possible for other DNA repair proteins to fill the gap and to seal the nicks. The in vitro experiments performed herein indicate that FEN-1 is capable of processing CDF.

To provide direct evidence of central DNA flap removal, Southern blotting of Hirt DNA (the DNA isolated from cytoplasm only) was performed to detect the accumulation of CDF in FEN-1 deficient cell lines. The single gap generated at the cPPT due to the formation of CDF in the plus strand leaves a site at the center of the minus strand of HIV-1 cDNA sensitive to SI nuclease. The cleavage on the minus strand by S1 nuclease generates two DNA fragments approximately 4.9-kb, while the processed and sealed plus strand prevents this cleavage, resulting in a DNA fragment of the full length HIV cDNA (9.7 Kb). Hirt DNA or HIV-1 cDNA present in cytoplasmic extracts was prepared from LaP, LaF and LaD cells infected with the VSV-G pseudotyped HIV-1 virus. The DNA was treated with S1 nuclease and resolved on an agarose gel, and Southern blotting was performed. Hirt DNA prepared from cells infected with a cPPT deficiency virus was used as a flap-minus control. The intensity of signals for those HIV-1 cDNA products was determined quantitatively to evaluate the FEN-1 mediated central DNA flap removal and the inhibition by dominant-negative expression of D181A. CDFs were processed in Hirt DNA purified from the wild type cell line infected with HIV-1, but not that from mutant cell lines that over-express D181A mutant FEN-1.

The cleavage of the minus strand by S1 nuclease validates the presence of nicks or gaps in the plus strand of HIV-1 cDNA. HIV-1 cDNA should be sensitive to the S1 nuclease cleavage only in infected cell lines with CDF-derived nicks or gaps. Moreover, the products of S1 nuclease cleavage represent the levels of synthesized HIV-1 cDNA in all three cell-lines, which is used in the comparison of CDF processing quantitatively. Since FEN-1 plays a critical role in the cleavage of HIV-1 central DNA flap and the cleavage happens in PICs, HIV-1 cDNA with processed CDF is detected predominantly in cells with the wild-type FEN-1 genetic backgrounds, LaP and LaF cells. Those with unprocessed CDF are seen in LaD cells, in which the wild-type FEN-1 mediated CDF cleavage is blocked due to the dominant negative effect of D181A mutant.

Nuclease assays. DNA model substrates were prepared as previously described (Zheng 2005). FEN-1 nuclease and/or D181A mutant was incubated with 1 pmol of indicated DNA substrates at 30° C. for 15 minutes. DNA substrates and products were separated in DNA sequencing PAGE and visualized with autoradiography.

Example 7

Impaired Processing of CDF due to FEN-1 Deficiency Leads to Failure of HIV Integration and Replication Impaired processing of CDF due to FEN-1 deficiency leads to failure of HIV integration and replication because HIV-1 virus with unprocessed CDF is not able to integrate efficiently. The HIV-1 central DNA flap has to be cleaved for a stable integration. Because FEN-1 is essential for the CDF cleavage, the HIV-1 integration intermediates with unprocessed CDF accumulate in the LaD cells. Such integration impairment leads to failure of virus replication. Genetically-engineered human cell lines that overexpress D181A are tested for the efficiency of HIV-1 integration and replication. Since it is unlikely that overexpression of D181A inhibits the entry of virus into the nucleus, the analysis focuses on HIV-1 integration and replication in the infected cells. By quantitatively detecting copy number of the integrated HIV-1 cDNA molecules in the human host genome, the experiment shows that HIV replication is inhibited.

This experiment demonstrates the effect of FEN-1 mediated CDF cleavage on HIV-1 integration by determining HIV-1 integration efficiency in parental, FEN-1 or D181A overexpressing cells. The cells are infected with a modified HIV-1 virus. Upon integration, the infected cells become hygromycin-resistant due to the expression of the drug-resistant gene from the proviral DNA. The integration efficiency is then determined by counting the colonies selected on Hygromycin B. The integration is confirmed by LTR-Tag assay.

A modified HIV-1 virus vector derived from strain HXB2 (HXB2-Hyg) with a newly created Bpm I site near the end of the U5 region in its 5' LTR is prepared. This virus genome also contains a hygromycin-resistant gene for selecting virus-infected cells. This VSV-G pseudotyped virus is used to infect LaD cells along with LaF and LaP cells with m.o.i. of 1.0. The infected cells are cultured in a medium containing 200 μg/ml of Hygromycin B for 2 weeks. The virus-infected cells with the stable integrated provirus are hygromycin-resistant and grow into colonies. The colonies are stained with 0.2% crystal violet in 10% phosphate-buffered formalin (pH 7.0) and counted.

To confirm the effects of FEN-1-driven CDF processing on integration, genomic DNA is prepared from the infected cells with different genetic backgrounds and used for LTR-Tag analysis. The method is based on the ability of a class II S restriction enzyme, Bpml, to cleave DNA at a defined distance of 16 base pairs downstream of its 5'-CTGGAG-3'

(SEQ ID NO: 1) recognition sequence. The new Bpm I site is copied to the end of the U5 region in the 3' LTR of the proviral DNA due to the retrovirus reverse transcription. The new site is positioned such that Bpm I is able to cut genomic DNA sequences at various integration sites when the proviral DNA is joined to chromosomes. The critical feature of this experimental design is that the new Bmp I cleavage site is created only where and after HIV is integrated into the host genome.

Figure 8:
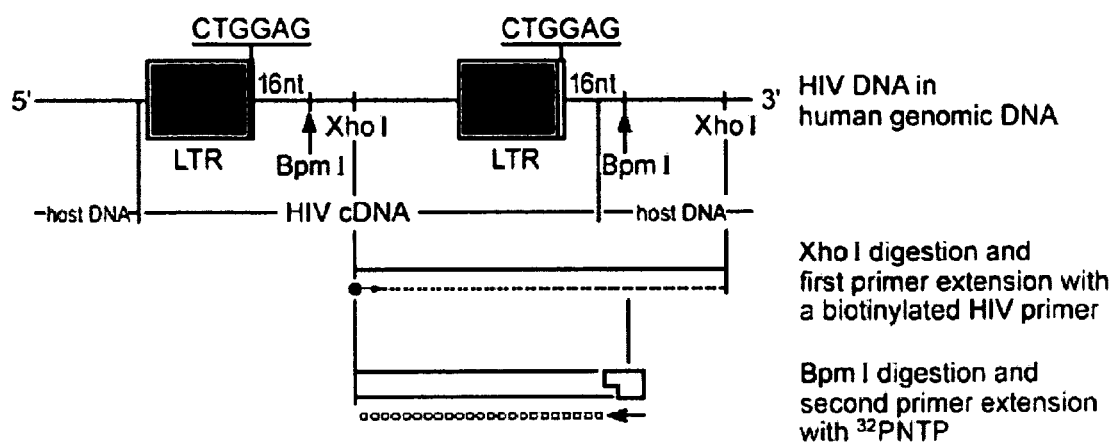
FIG. 8 is a diagram showing quantification of integrated HIV molecules in host genomes. The first primer extension purifies HIV DNA from digested total genomic DNA, while the second primer extension quantifies the integrated HIV molecules.
Figure 9:
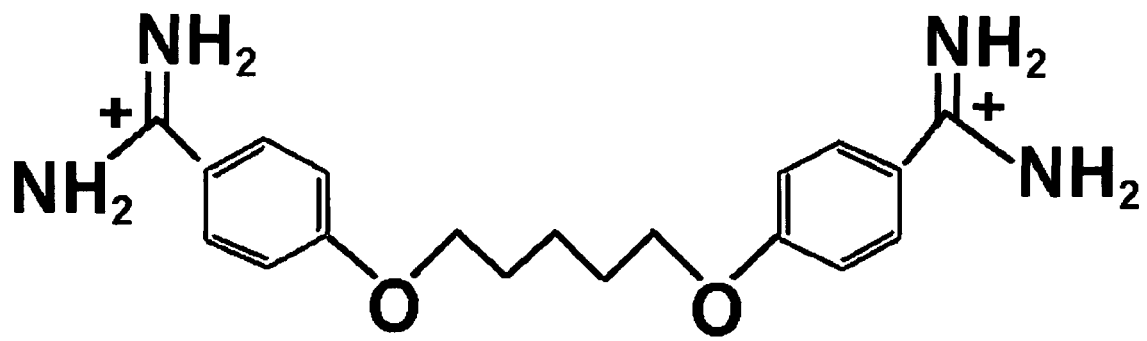
FIG. 9 is a structural representation of pentamidine ($C_{19}H_{24}N_4O_2$), a dication organic molecule with two aromatic groups.
Figure 10:
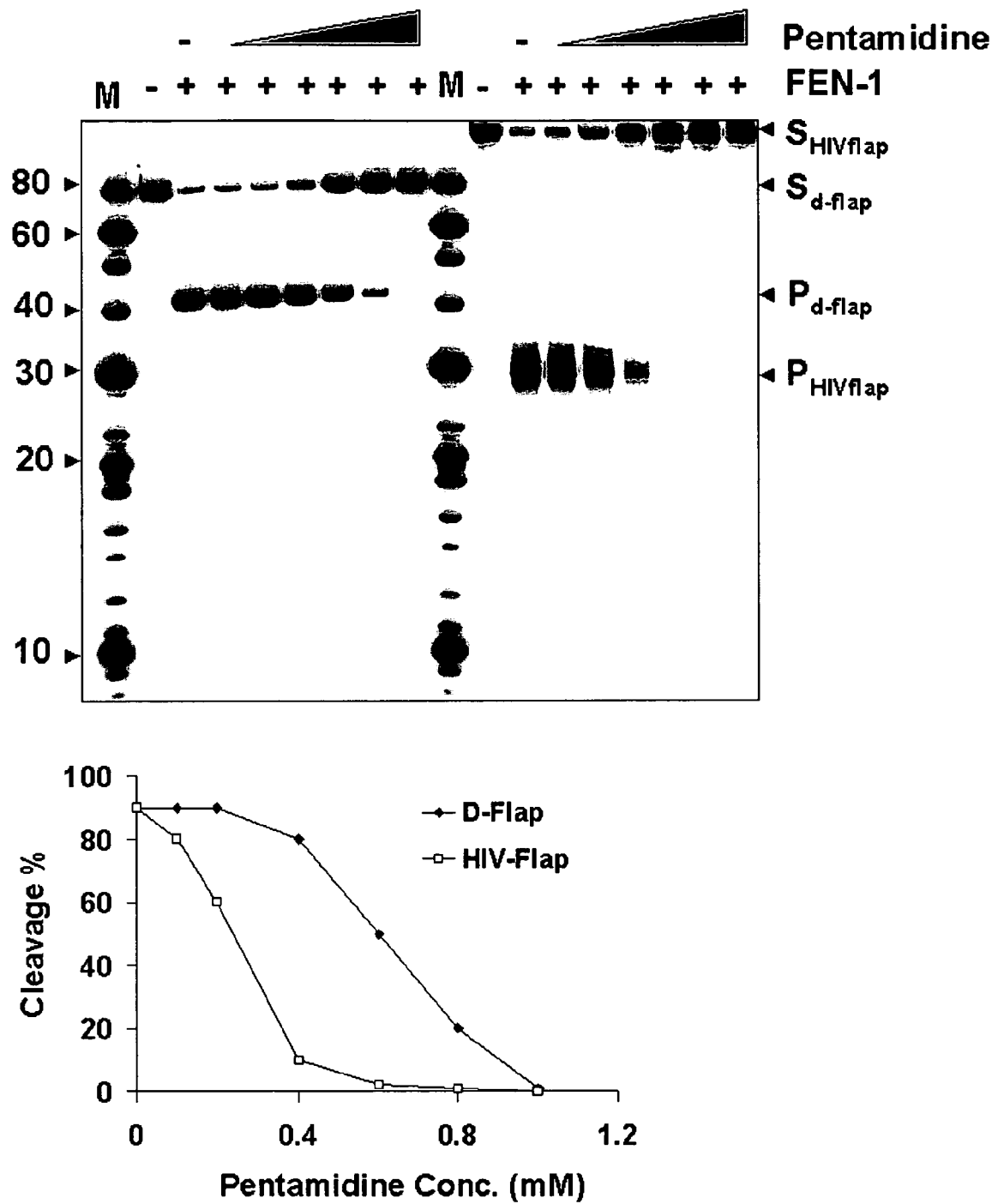
FIG. 10 is a gel and a line graph showing concentration-dependent inhibition of pentamidine on FEN-1 cleavage of HIV CDF or regular 5' flap substrates. 0.25 or 0.5 pmol of purified recombinant FEN-1 were mixed with 1 pmol of regular 5' flap substrate with a 3' flap of single nucleotide or HIV CDF substrate, respectively in the presence of 0, 0.1, 0.2, 0.4, 0.6, 0.8, and 1.0 mM pentamidine isethionate salt. The reaction was carried out at 37° C. for 30 minutes. Substrates and products were analyzed with DNA sequencing PAGE and visualized with radio-autograph (upper panel). The amount of cleavage products and non-cleaved substrates were quantified with ImagineQuant and were shown in the bottom panel.
Figure 11:
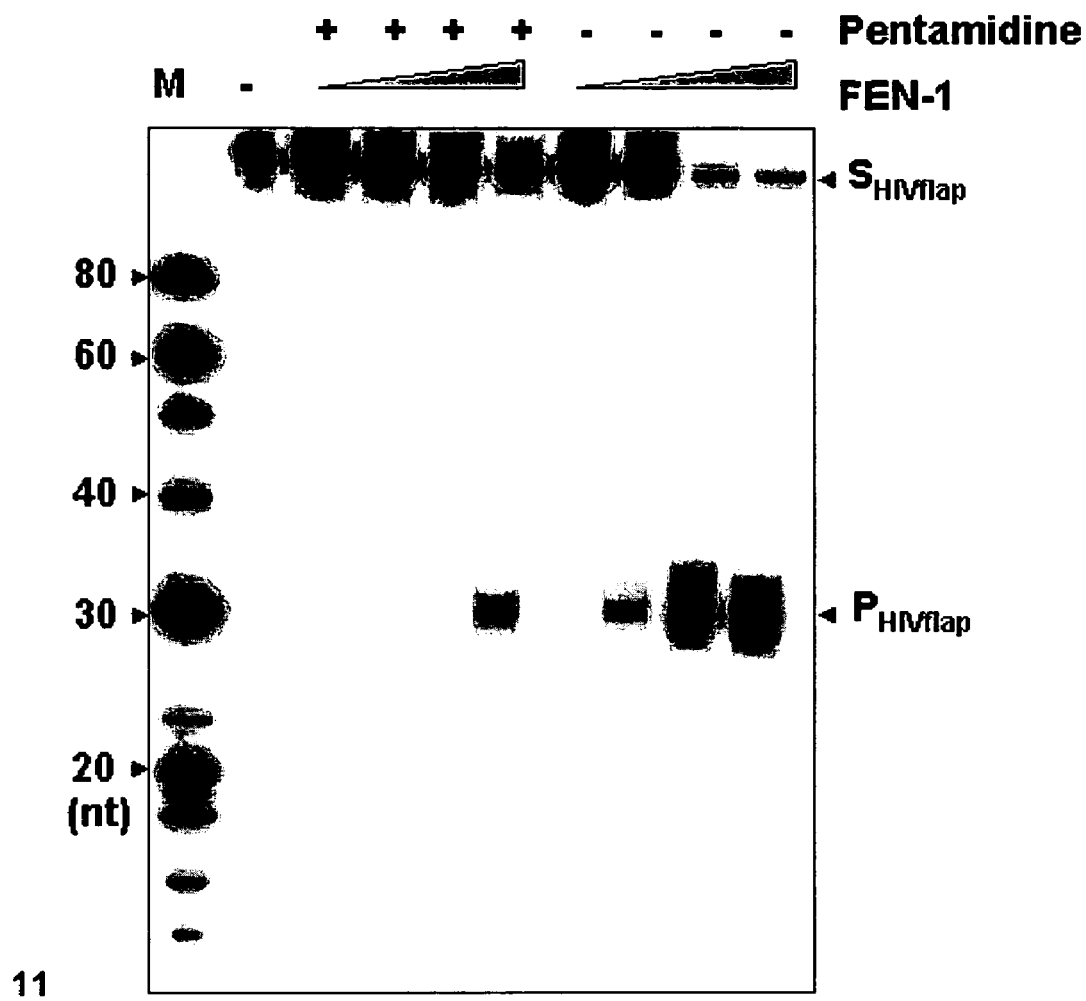
FIG. 11 is a gel and a line graph showing FEN-1 concentration-dependent cleavage of HIV CDF substrate in the absence or presence of pentamidine. One pmol of HIV CDF substrate were mixed with 0, 0.01, 0.1, 1, and 3 pmol of purified recombinant FEN-1 in the absence or presence of 0.4 mM pentamidine isethionate salt. The reaction was carried out at 37° C. for 30 minutes. Substrates and products were analyzed with DNA sequencing PAGE and visualized with radio-autograph (upper panel). The amount of cleavage product and non-cleaved substrate were quantified with Imagine-Quant and were shown in the bottom panel.
Figure 11:
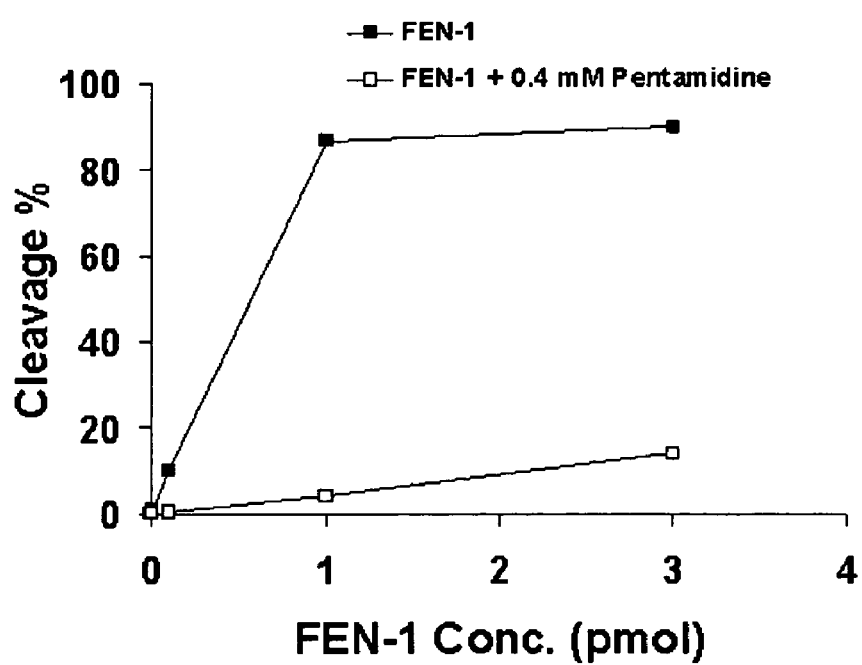
Figure 12:
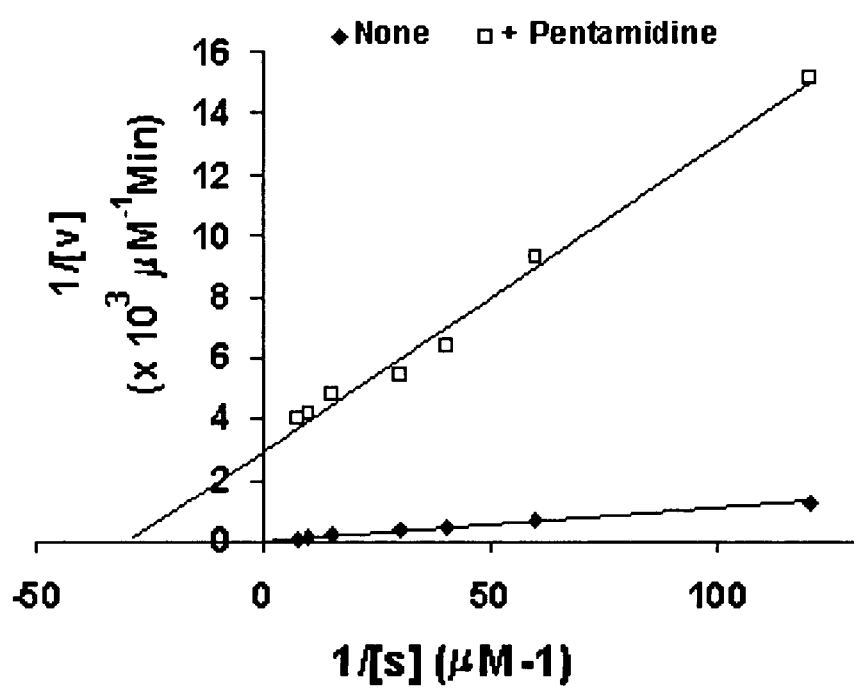
FIG. 12 is a graph line and chart showing kinetic analysis of FEN-1 cleavage of HIV CDF substrates in the absence and presence of pentamidine. 1 pmol of FEN-1 was incubated with 0, 0.125, 0.25, 0.375, 0.5, 1, and 2 pmol of HIV CDF substrates. The reaction were carried out at 37° C. for 10 min. The amount of cleavage product and non-cleaved substrate were quantified with ImagineQuant. The Michaelis-Menten kinetic parameters $K_m$ and $K_{cat}$ (Bottom panel) were calculated with double-reciprocal plots of 1/v versus 1/[s] (Upper panel).

To generate LTR-Tag, the genomic DNA is first linearized with XhoI, which has only one recognition site on the HIV sequence. The digested DNA is subjected to the first primer extension using a biotinylated oligonucleotide primer, specific to the HIV-1 genome. The products of the HIV-specific primer extension are enriched and purified with a streptavidin column. Bpm I will then digest the enriched DNA and the digested DNA is ligated to a double-stranded oligonucleotide linker for a second primer extension (FIG. 8). By then, the integrated HIV DNA molecules are tagged (LTR-Tags). During the second primer extension, $^{32}$P-α-dCTP is incorporated. The radioactivity incorporation should be proportional to the amounts of integrated HIV-1 provirus. The amount of integrated HIV-1 proviral DNA is then determined by detecting $^{32}$P radioactivity.

Cells that do not have an integrated provirus are unable to sustain growth under antibiotic selection for 2 weeks. A stable integration of HIV-1 DNA is required for the virus-infected cells to become hygromycin-resistant. Under these conditions, hygromycin-resistant colonies are consistently found on plates of the infected LaF and LaP cells. The integration in the LaD cells, however, is inhibited due to the D181A-mediated block of the CDF removal, resulting in far fewer hygromycin-resistant colonies.

Figure 14:
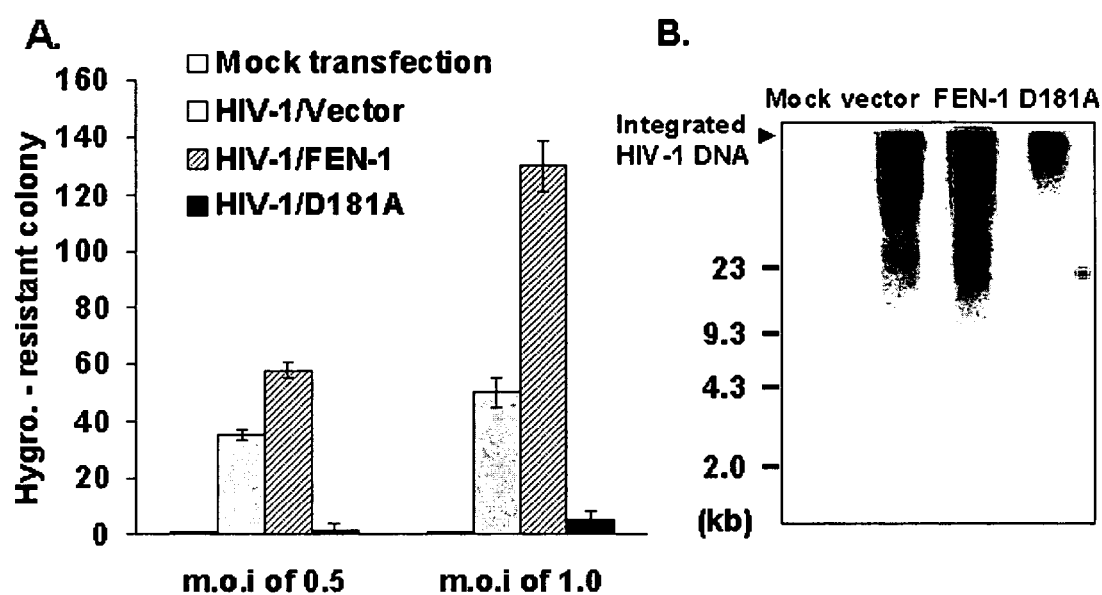
FIG. 14 shows that FEN-1 activity is required for HIV-1 integration. (A) Hygromycin-resistant colony assay. HeLa cells were infected with HXB2-Hyg at multiplicity of infection (m.o.i.) of 0.5 and 1.0. Values were the meansjstd colonies of 5 independent assays. (B) Detection of HIV-1 provirus. Host genomic DNA was prepared and integrated HIV cDNA was detected with Southern blot hybridization using probe that is specifically complementary to HIV-1 cDNA.

An LTR-Tag analysis method is used to detect HIV integration. HIV-1 LTR-Tag is generated from three different DNA sequences: a fragment of 3' LTR, a 14-bp genomic DNA from an integration site, and the linker. The generation of LTR-Tags is dependent on the FEN-1-mediated CDF processing and the completion of integrase-mediated HIV-1 integration. If the central DNA flap has not been removed, or nicks and gaps at the cPPT site are not filled or sealed, integration are impaired. Therefore, LTR-Tag will not be generated due to the failure of integration. Bound on the overlaps in the CDF, D181A is able to strongly inhibit the wild-type hFEN-1 or other FEN-1-like proteins flap-cleavage activity. For this reason, there are many fewer $^{32}$P-labeled LTR-Tags prepared from the D181A overexpressing LaD cells in comparison to the radioactivity-labeled LTR-Tags prepared from the LaP cells. An HIV-1 infection colony assay was conducted by challenging different engineered HeLa-CD4+ cells with a modified HIV-1 vector, HXB2-Hyg, in which a hygromycin gene is fused to the 3' end of HIV-1 pol gene (Gaur 1998). Therefore, the expression of hygromycin depends on the stable integrated HIV-1 provirus, correlating the survival of cells [hygromycin-resistant colony forming unit (CFU)] and the integration of HIV-1 in vivo. The results revealed that expression of D181A decreased HIV-1 integration by more than 95% CFUs compared to control HeLa CD4+ cells (FIG. 14A). Over-expression of exogenous wild-type hFEN-1 increased CFUs greater than 2.5 fold at an m.o.i of 1.0 (FIG. 14A), consistent with the suggestion that FEN-1 plays an important role in HIV integration.

To further validate that inhibition of FEN-1 nuclease activity reduced HIV-1 cDNA integration, genomic DNA was isolated and the integration of viral cDNA into the host genome was detected by Southern blot hybridization. Consistent with the previous observation, expression of exogenous wild type FEN-1 enhanced HIV-1 cDNA integration, but expression of D181A significantly decreased the integration (FIG. 14B). Both of the experiments indicate that the integration of HIV may be impaired under a FEN-1 deficient background.

HIV-1 integration assay. Genomic DNA was isolated from HIV-1 infected cells according to a previous protocol (Chen 1998). 20 μg of DNA was digested with EcoRV and BamHI and resolved on a native agarose gel. A 0.8 kb of HIV-1 specific DNA fragment, released by digestion of HIV cDNA with BamHI and BglIII, was used as a probe in Southern blot hybridization.

HIV-1 infection colony assay. HeLa cells, or HeLa cells expressing the c-myc-tagged hFEN-1 or D181A, were seeded at $0.5 \times 10^4$ cells per well in a 6-well plate. The HIV-1 vector HXB2-Hyg was added at m.o.i. of 0.5. The infection was allowed for six hours and the cells were rinsed three times with 1 ml of fresh medium. The cell was cultured for 36 hours before being fed with medium containing 200 μg/ml of hygromycin B. Cultures were maintained for two weeks, with medium changes every 4-5 days. Hygromycin-resistant colonies were stained with 0.2% crystal violet in 70% ethanol, and the number of colonies was counted.

Example 8

Reverse Transcriptase Activity Profile

HIV-1 virus replication is inhibited in CEM cells which overexpress D181A FEN-1 mutant. The lack of CD4 receptor on the HeLa cell membrane makes it impossible for HIV-1 virus to spread, which limits investigation of HIV-1 replication inhibition by D181A. The CEM cell line, a CD4 positive human cell line derived from T cell lymphoma, is permissive for studying HIV-1 infection and virus replication. The cell is engineered for D181A overexpression and infected with replication competent HIV-1. As virus replicates in the infected cells, new viral particles are released into the medium. Endogenous RT assay is performed to examine HIV-1 replication and virus replication profiles are established. A reverse transcriptase activity profile is established to show that HIV-1 replication is inhibited in FEN-1 deficient T-cell lines.

In order to study the end consequence of FEN-1 deficiency to the HIV-1 replication, human CEM lymphocytes with hFEN-1 or D181A overexpressing plasmid have been transfected. CeFEN-1 is designated for CEM cells overexpressing FEN-1, while CeD181 A is for CEM cells overexpressing D181A ("D181A dominant negative CEM cells"). The transfectants were selected on G418 for two months, after which the G418-resistant cells were pooled and cell extracts prepared. The expression of exogenous FEN-1 or D181A was determined with Western blotting using the anti-FEN-1 antibody and the anti-c-myc antibody. Single-cell cultures were isolated to clone the D181A overexpressing cell lines. Both heterogeneous and homogeneous cells were used in this experiment.

To accomplish HIV-1 virus infection, $0.5 \times 10^5$ of the modified CEM cells expressing the c-myc tagged FEN-1 or D181A were infected with the wild-type HIV-1 virus stain NL4-3 at m.o.i. of 0.05. After four hours post-infection, the virus-containing medium was removed and the cells were rinsed before incubating in fresh medium. The culture medium was collected every 24 hours and centrifuged to precipitate cell debris. The medium was collected every two days for 2 weeks after infection. Virion were precipitated and collected.

The endogenous reverse transcriptase (RT) assay is modified from a procedure described by Sharma and Crumpacker (Sharma 1999). Virion lysates were used in the reverse transcription reaction, containing Tris (pH 7.8)-based buffer, dNTPs (dCTP, dGTP, and dTTP) and $^{32}$P-α-dATP. The reaction was carried out at 37° C. for 4 hours and extracted with phenol-chloroform followed by ethanol precipitation. The precipitated cDNA was spotted on a piece of Whatman GF/C glass fiber filter membrane and exposed to the X-ray film and quantified by liquid scintillation counting. Equal radioactivity counts of the RT reaction products are separated on a 1% alkaline denaturing agarose gel. The RT cDNA products are visualized by autoradiography, and scanned for the intensity of α-$^{32}$P by using the ImageQuant (Molecular Dynamics) software. Then, virus replication profiles are established by measuring the endogenous RT activity for an entire 14-day infection period.

The endogenous RT assay is performed to test HIV-1 replication in human CD4 positive T-lymphocytes. The designed endogenous RT assay has the following advantages: 1) use of natural primers; 2) the retrotranscription that is composed in RNA-dependent DNA polymerase reaction, RNase H nuclease cleavage, and DNA-dependent DNA polymerase reaction is expressed in an ordered fashion; and 3) the retrotranscription takes place in a complex in which all viral proteins are present. Since the infectious virus titer is known, the actual reaction rate per virion provided that the number of infectious virus and the virus capable of retrotranscription in vitro are comparable. After infection, the replicating virus requires a stable integration of HIV-1 cDNA and efficient expression of proviruses in the infected cells. Regardless of the integration efficiency in CeFEN-1 and CeD181A cells, HIV-1 replication in D181A overexpressing cells is impaired in comparison to the FEN-1 overexpressing cells. Virus replication profiles are established by measuring the endogenous RT activity for an entire 14-day infection period. If the FEN-1 mediated CDF cleavage is required, the HIV-1 replication profiles between WT and FEN-1 deficient cell lines will have different patterns: one displaying a diminished HIV-1 virus production while the other steadily increasing the viral particles.

Endogenous reverse transcription assay. 5×10$^5$ HeLa cells expressing the c-myc tagged hFEN-1 or D181A were infected with the replication competent HIV-1 virus NL4-3 at m.o.i. of 0.1 (equivalent to 20 ng of p24 protein). Four hours post-infection, the virus-containing medium was removed and the cells were washed three times with 5 ml of fresh medium before being returned for growth. The culture medium was collected every 24 hours and spun 5 minutes to precipitate cell debris. Virions were precipitated by incubating 1 ml of the culture medium with 500 μl of 30% PEG 8,000/500 mM NaCl at 4° C. overnight. The precipitates were centrifuged at 3,500 rpm and 4° C. for 30 min. Virion pellets were resuspended in 25 μl of Buffer K supplemented with 0.025% digitonin. The virion lysates were incubated on ice for 30 min. An endogenous reverse transcriptase (RT) assay was conducted following a procedure described by Sharma and Crumparker (Sharma 1999). Reactions were analyzed by autoradiography and quantified by ImageQuant. Virus stock equivalent to 1 ng of p24 protein was used as a standard in the assay.

Example 9

Identification of FEN-1 Inhibitors

While FEN-1 simply uses its FEN activity to cleave RNA-DNA primers, FEN-1 may need both FEN and GEN activities to resolve HIV CDF due to the formation of stable secondary structures in the 99 nucleotide HIV CDF. Thus, any FEN-1 inhibitor that suppresses only GEN activity but not FEN activity may specifically inhibit the FEN-1-mediated HIV CDF cleavage but have little effect on the FEN-1 cleavage of the 5' DNA flap substrates resembling RNA-DNA primer structures.

The FEN-1 active center consists of two magnesium ions and six residues, E34, D86, E160, D179, D181, and D238 coordinating with the magnesium ions. Substitution of any of the six essential negative-charged amino acid residues with an Ala residue eliminates FEN-1's FEN, 5' exo, and GEN activities. Substitution of negative-charged residue E178, which is in the vicinity of the active center instead of direct binding to the magnesium ion, with an Ala residue only eliminates FEN-1's GEN activity but not the FEN activity. Thus, introduction of limited interference to the negative charge network within FEN-1's active center and its vicinity, by addition of positive-charged small molecules, causes the enzyme losing the GEN activity but not FEN activity similar to that shown in the E178A mutant.

To screen and determine inhibitors that suppress FEN-1 processing HIV-CDF model structures in vitro, small molecules that pass all three consecutive tests are subjected to in vivo experimentation. All small molecules screened during this experiment are commercially available, but this method is equally applicable to novel or proprietary molecules.

The first criteria is an assessment of molecular charge. Positive-charged organic molecules, particularly, the dication organic molecules, whose two positive charges are approximately 5 angstrom apart mimicking the distance between two $Mg^{2+}$ in the active center, are qualified. Dication metal ions, including $Ca^{2+}$, $Co^{2+}$. $Cu^{2+}$, $N^{i2+}$, and $Zn^{2+}$ are not qualified, because they significantly inhibit both FEN and GEN activities.

Molecules passing criteria 1 are subjective to criteria 2, which is molecular structure. Positively-charged molecules that have at least one aromatic or imidazol group are qualified. The aromatic or imidazol group within the molecules interacts with the aromatic side chains in FEN-1's active center and its vicinity through the hydrophobic interaction. Thus, these kinds of molecules interact with FEN-1 better than those without aromatic or imidazol group.

Finally, the third criteria is in vitro inhibition of HIV-CDF processing. The inhibition of FEN-1 cleavage of HIV-CDF and regular 5' flap structures by molecules selected after criteria 2 are examined in this test. Only the molecules that inhibit FEN-1 cleavage of HIV-CDF but not the regular 5' flap structures are qualified for in vivo studies. The inhibition efficacy of HIV replication in H9 and CEM T cell lines by small molecules is determined with the HIV reverse transcriptase inhibitor AZT used as an inhibition control.

With the three criteria defined above, a dication organic molecule, pentamidine (FIG. 9) was successfully identified to be a potential drug that inhibits FEN-1 processing HIV CDF. Nuclease assays indicated that in the presence of 400 μM of pentamidine, 90% of the FEN-1 cleavage of HIV CDF structures was suppressed, but greater than 80% of FEN-1's activity cleaving regular 5' flap substrates was retained (FIG. 10 and 11). At concentrations higher than 1 mM, cleavage of both HIV CDF and regular 5' flap substrates was completely inhibited. Kinetic analysis revealed that pentamidine decrease the kcat and Km of FEN-1 cleavage of HIV CDF substrates, showing that binding of pentamidine to FEN-1 adversely affect the catalysis but increase the enzyme's affinity to the substrate (FIG. 12).

Example 10

Pentamidine Inhibits HIV Replication In Vivo

Figure 13:
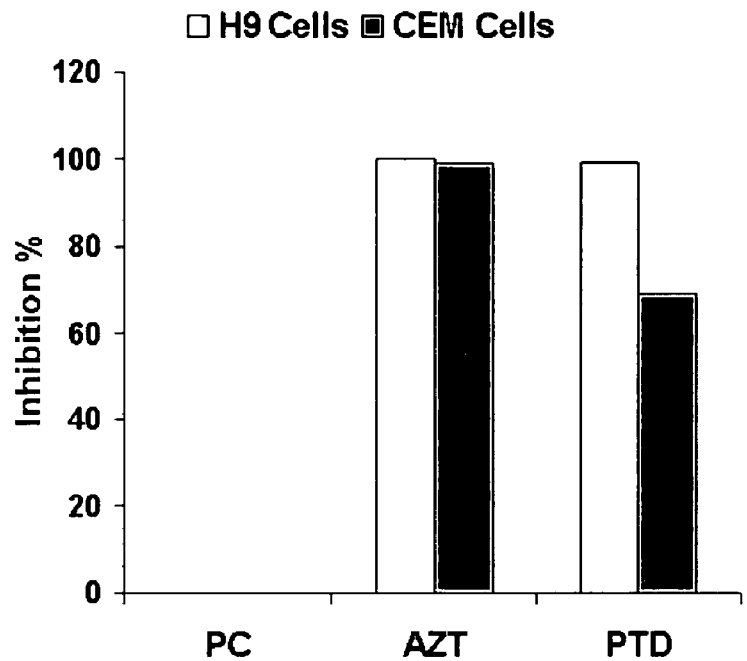
FIG. 13 shows that pentamidine (PTD) is equal to or more effective than AZT in inhibiting HIV replication.
Figure 13:
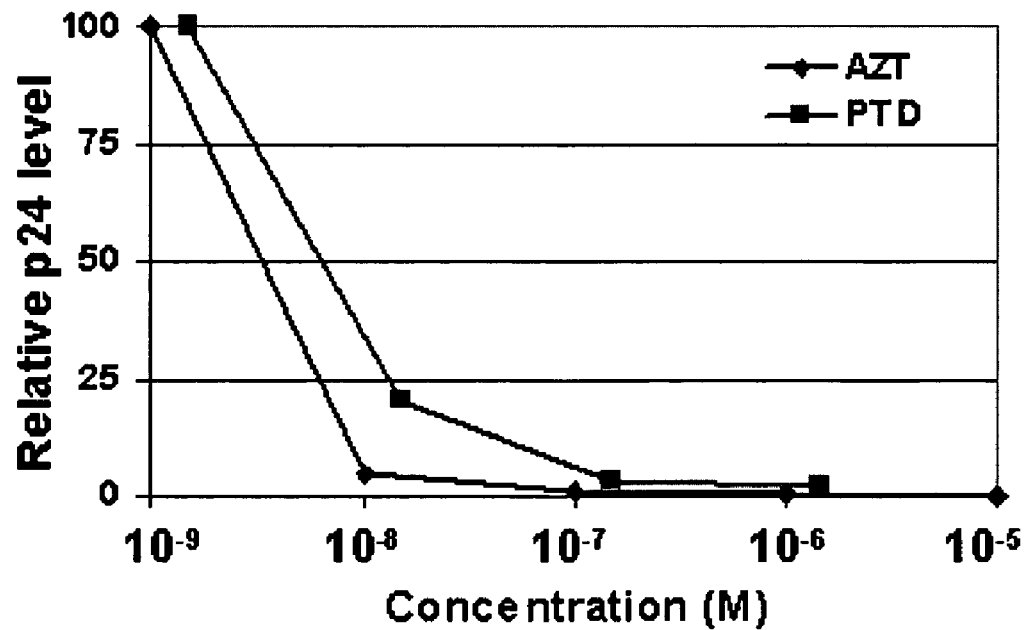

The next experiment examined whether pentamidine could inhibit HIV replication in vivo. The H9 cells and CEM cells were challenged with HIV IIIB virus in the absence or presence of 15 µM pentamidine or 10 µM AZT, a HIV reverse transcriptase inhibitor. Pentamidine significantly inhibited HIV replication in both cell lines. Pentamidine suppressed HIV replication in H9 cells and CEM cells by 98.8% and 69.3%, respectively, while AZT inhibited HIV replication in H9 cells and CEM cells by 100% and 98.6%, respectively (FIG. 13). Thus, pentamidine is a novel and effective HIV replication inhibitor.

Cytotoxicity assay: All cell-based assays must determine whether non-specific cytotoxicity is present in the culture during the confirmatory anti-HIV challenge experiments. Cell used in an assay are evaluated using a standard commercial cytotoxicity assay kit (Promega) to assess cytotoxicity (Decker 1988). At day four of culture (or the anticipated peak day for HIV observations), 50 ul culture supernatant is mixed with 50 ul lactate substrate in 96-well plate. Lactate dehydrogenase (LDH) is released into the supernatant by toxic cells and is measured with a 30-minute coupled enzymatic assay, which results in the conversion of a tetrazolium salt into a red formazan product. A culture control is included in quadruplicate, and cytotoxicity is defined at absorbance values of test culture that is 2 standard deviations above the mean for the control.

Antiviral challenge assays using infectious laboratory and other HIV-1 strains: Appropriate cells, screened for viability and growth kinetics, are challenged with HIV-1 strain IIIB, NL4-3, JRFL or primary isolates. This is a modification of a standard method described by Ho (Ho 1991) for virus neutralization. The resultant inoculum is titrated by $ID_{50}$ in uninfected CEM, H9 or PBMC cultures. 0.01 MOI HIV is inoculated onto $10^6$ candidate cells for six hours at 37° C., and then washed three times with PBS. For screening assays, each cell culture supernatant is examined on day seven post infection and examined for reverse transcriptase activity or p24 concentration. For confirmation assays, cultures are followed for day 7, 14, 21 and 28 observations. Cells are fed twice weekly by removing one-half of the media. Viral inhibition is defined >50% reduction in RT activity or p24 compared with control culture, which were mock-treated.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

REFERENCES CITED

1. Bushman, F. D. 1999. Host proteins in retroviral cDNA integration. *Adv. Virus Res.* 52:301-317.
2. Charneau, P., and Clavel, F. (1991) A single-stranded gap in human immunodeficiency virus unintegrated linear DNA defined by a central copy of the polypurine tract. *J. Virol.* 65:2415-2421.
3. Charneau, P., Alizon, M., and Clavel, F. (1992) A second origin of DNA plus-strand synthesis is required for optimal human immunodeficiency virus replication. *J. Viol.* 66:2814-2920.
4. Charneau, P., Mirambeau, G., Roux, P., Paulous, S., Buc, H. and Clavel, F. (1994) HIV-1 reverse transcription. A termination step at the center of the genome. *J. Mol. Biol.* 241, 651-62.
5. Chen, H., and Engelman, A. (1998) The barrier-to-autointegration protein is a host factor for HIV type 1 integration. *Proc. Natl. Acad. Sci. USA*. 95:15270-15274.
6. Coffin, J. M., Hughes, S. H., et al., (1997) Retroviruses. New York, Cold Springs Harbor Press.
7. Decker, T., and M. L. Lohmann-Matthes. 1988. A quick and simple method for the quantitation of lactate dehydrogenase release in measurements of cellular cytotoxicity and tumor necrosis factor (TNF) activity. *J Immunol Methods* 115:61-9.
8. Doranz, B. J., Bail, S. S. et al., (1999) Use of a gp 120 binding assay to dissect the requirements and kinetic of human immunodeficiency virus fusion events. *J. Viol.* 73,10346-10258.
9. Dvoin, J. D., Bell, P., Maul, G. G., Yamashita, M., Emerman, M., and Malim, M. H. (2002) Reassessment of the role of integrase and the central DNA flap in human immunodeficiency virus type 1 nuclear import. *J. Virol.*, 76,12087-12096.
10. Farnet, C. M., and Haseltine, W. A. (1990) Integration of human immunodeficiency virus type 1 DNA in vitro. *Proc. Natl. Acad. Sci. USA* 87:4164-4168.
11. Farnet, C. M. and Haseltine, W. A. (1991) Determination of Viral proteins present in the human immunodeficiency virus type 1 preintegration complex. *J. Viol.* 65,1910-1915.
12. Farnet, C. M., and Bushman, F. D. (1997) HIV-1 cDNA integration: requirement of HMG I(Y) protein for function of preintegration complexes in vitro. *Cell* 88:483-492.
13. Faust, E. A. and Triller, H. (2002) Stimulation of human flap endonuclease 1 by human immunodeficiency virus type 1 integrase: Possible role for flap endonuclease 1 in 5'-end processing of human immunodeficiency virus type 1 integration intermediates. *J. Biomedical Science*, 9,273-287.
14. Gaur, M., and A. D. Leavitt. 1998. Mutations in the human immunodeficiency virus type 1 integrase D,D(35)E motif do not eliminate provirus formation. *J. Virol.* 72:4678-85.
15. Ho, D. D., J. A. McKeating, X. L. Li, T. Moudgil, E. S. Daar, N. C. Sun, and J. E. Robinson. 1991. Conformational epitope on gp120 important in CD4 binding and human immunodeficiency virus type 1 neutralization identified by a human monoclonal antibody. *J Virol* 65:489-93.
16. Hungnes, O., Tjotta, E. and Grinde, B. (1992) Mutations in the central polypurine tract of HIV-1 result in delayed replication. *Virology* 190, 440-442.
17. Kao, H.-I., and Bambara, R. A. (2004) The protein components and machanism of eukaryotic Okazaki fragment maturation. Critical Reviews in *Biochemistry and Molecular Biology*, 38,433-452.
18. Kucherlapati, M., Yang, K., Kuraguchi, M. et al., (2002) Haploinsufficiency of flap endonuclease (Fen-1) leads to rapid tumor progress. *Proc. Natl. Acad. Sci. USA*, 99,9924-9929.
19. Lieber, M. R. (1997) The Fen-1 family of structure-specific nucleases in eukaryotic DNA replication, recombination and repair. *BioEssays*. 19, 233-240.
20. Limón, A., Nakajima, N., Lu, R., Ghory, H. Z. and Engelman, A. (2002) Wild-type levels of nuclear localization and human immunodeficiency virus type 1 replication in the absence of the central DNA flap. *J. Virol.* 76:12078-12086.

21. Miller, M. D., Wang, B.-B. and Bushman, F. D. (1995) Human immunodeficiency virus type 1 preintegration complexes containing discontinuous plus strand are competent to integrate in vitro. *J. Virol.* 69:3938-3944.

22. Miller, M. D., Farnet, C. M. and Bushman, F. D. (1997) Human immunodeficiency virus type 1 preintegration complexes: studies of organization and composition. *J. Virol.* 71:5382-5390.

23. Murante, R. S., Rust, L. and Bambara, R. A. (1995) Calf 5' to 3' exo/endonuclease must slide from a 5' end of the substrate to perform structure-specific cleavage. *J. Biol. Chem.* 270, 30377-83.

24. Qiu, J., Li, X., Frank, G., and Shen, B. (2001) Cell cycle-dependent and DNA damage-inducible nuclear localization of FEN-1 nuclease is consistent with its dual functions in DNA replication and repair. *J. Biol. Chem.*, 276, 4901-4908.

25. Rumbaugh, J. A., Fuentes, G. M. and Bambara, R. A. (1998) Processing of an HIV replication intermediate by the human DNA replication enzyme FEN1. *J. Biol. Chem.* 273, 28740-5.

26. Sambrok et al. 2001. Molecular Cloning: A Laboratory Manual, 3$^{rd}$ Edition. Cold Spring Harbor Press, Cold Spring Harbor, N.Y.

27. Sharma, P. L, and Crumpacker, C. S. (1999) Decreased processivity of human immunodeficiency virus type 1 reverse transcriptase (RT) containing didanosine-selected mutation Leu74Val: a comparative analysis of RT variants Leu74Val and lamivudine-selected Met184Val. *J. Virol.* 73:8448-856.

28. Shen, B., Nolan, J. P., Sklar, L. A. and Park, M. S. (1996) Essential amino acids for substrate binding and catalysis of human flap endonuclease-1. *J. Biol. Chem.* 271, 9173-9176.

29. Shen, B., Qiu, J., Hosfield, D. and Tainer, J. A. (1998) Flap endonuclease homologues in archaebacteria exist as independent proteins. *TiBS.* 23,171-173.

30. Shibata, Y., and Nakamura, T. (2002) Defective flap endonuclease 1 activity in mammalian cells is associated with impaired DNA repair and prolonged S phase delay. *J. Biol. Chem.* 277:746-754.

31. Stevenson, M. (2000) HIV nuclear import: What's the flap? *Nat. Med.* 6, 626-8.

32. Whitwam, T., Peretz, M. and Poeschla, E. (2001) Identification of a central DNA flap in feline immunodeficiency virus. *J. Virol.* 75, 9407-14.

33. Yam, P. Y., S. Li, J. Wu, J. Hu, J. A. Zaia, and J. K. Yee. 2002. Design of HIV vectors for efficient gene delivery into human hematopoietic cells. *Mol Ther* 5:479-84.

34. Yoder, K. E., and Bushman, F. D. (2000) Repair of gaps in retroviral DNA integration intermediates. *J. Virol.* 74, 11191-11200.

35. Zennou, V., Petit, C., Guetard, D., Nerhbass, U., Montagnier, L. and Charneau, P. (2000) HIV-1 genome nuclear import is mediated by a central DNA flap. *Cell.* 101, 173-85.

36. Zennou, V., Serguera, C., Sarkis, C., Colin, P., Perret, E., Mallet, J. and Charneau, P. (2001) The HIV-1 DNA flap stimulates HIV vector-mediated cell transduction in the brain. *Nat. Biotechnol.* 19, 446-50.

37. Zheng, L., et al. (2005) Novel function of the flap endonuclease-1 complex in processing stalled DNA replication forks. *EMBO Reports,* 6:83-89.

---

---

The invention claimed is:

1. A method of screening for a FEN-1 inhibitor that inhibits HIV-specific replication, comprising:
   (a) identifying one or more FEN-1 inhibitor candidates that are small organic molecules identified by the following criteria:
      (i) a positive charge; and
      (ii) a molecular structure that has at least one aromatic group;
   (b) contacting an HIV-infected host cell with the one or more FEN-1 inhibitor candidates;
   (c) determining the efficacy of the one or more FEN-1 inhibitor candidates for inhibiting FEN-1 cleavage of HIV-central DNA flap (HIV-CDF) and/or inhibiting cellular 5' DNA flap structures; and
   (d) selecting one or more FEN-1 inhibitor candidates that inhibit FEN-1 cleavage of HIV-CDF but do not inhibit cellular 5' DNA flap structures.

2. The method of claim 1, wherein the one or more FEN-1 inhibitor candidates are dication organic molecules.

3. The method of claim 2, wherein positive charges of the dication organic molecule are approximately 5 angstroms apart.

4. The method of claim 1, wherein the aromatic group of the one or more FEN-1 inhibitor candidates is an imidazol group.

5. The method of claim 1, wherein the at least one aromatic group of the dication organic molecule interacts with one or more aromatic side chains of FEN-1.

6. The method of claim 1, wherein the efficacy of the one or more FEN-1 inhibitor candidates selected in step (d) is tested in comparison to the inhibitory activity of AZT or pentamidine.

7. The method of claim 1, wherein the efficacy of the one or more FEN-1 inhibitor candidates selected in step (d) is tested in comparison to the inhibitory activity of a FEN-1 dominant negative mutant.

8. The method of claim 7, wherein the FEN-1 dominant negative mutant is D181A.

9. The method of claim 1, wherein the efficacy of the one or more FEN-1 inhibitor candidates is tested by using a nuclease assay, chromatin immunoprecipitation assay, or a secreted protein assay.

10. The method of claim 1, wherein the one or more FEN-1 inhibitor candidates are screened at varying concentrations.

11. The method of claim 10, wherein the concentrations are selected from the group consisting of 100 μM, 500 μM, and 1 mM.

12. The method of claim 1, wherein the FEN-1 inhibitor selected inhibits replication of HIV-1.

13. A method of screening for a FEN-1 inhibitor that suppresses HIV-specific-replication, comprising the steps of:
   a) selecting one or more FEN-1 inhibitor candidates that are dication organic molecules having at least one aromatic group;
   b) incubating an HIV-infected cell with the one or more FEN-1 inhibitor candidates from step a);
   c) determining the efficacy of the one or more FEN-1 inhibitor candidates to inhibit FEN-1 cleavage of HIV-CDF and regular 5' flap structures; and
   d) selecting a FEN-1 inhibitor that inhibits FEN-1 cleavage of HIV-CDF but does not inhibit cellular 5' DNA flap structures.

14. The method of claim 13, wherein the aromatic group is an imidazol group.

15. The method of claim 13, wherein the efficacy of the one or more FEN-1 inhibitor candidates used in step c) is determined by using a nuclease assay, chromatin immunoprecipitation assay, or a secreted protein assay.

* * * * *